United States Patent [19]
Bruice et al.

[11] Patent Number: 6,013,785
[45] Date of Patent: Jan. 11, 2000

[54] POLYNUCLEOSIDE CHAIN HAVING MULTIPLE RIBONUCLEOSIDES, THE NUCLEOSIDES COUPLED BY GUANIDYL LINKAGES

[75] Inventors: Thomas C. Bruice; Robert O. Dempcy, both of Santa Barbara, Calif.; Orn Almarsson, Waterton, Mass.

[73] Assignee: The Regents of The University of California, Oakland, Calif.

[21] Appl. No.: 08/582,326

[22] Filed: Jan. 5, 1996

Related U.S. Application Data

[63] Continuation-in-part of application No. 08/268,859, Jun. 30, 1994, Pat. No. 5,696,253.
[51] Int. Cl.[7] .................................................. C07H 21/02
[52] U.S. Cl. .............................. 536/24.5; 514/43; 514/44
[58] Field of Search ............................ 536/24.5; 514/43, 514/44

[56] References Cited

U.S. PATENT DOCUMENTS

| | | | |
|---|---|---|---|
| 4,999,421 | 3/1991 | Brunck et al. | 530/350 |
| 5,141,849 | 8/1992 | Chou | 435/6 |
| 5,264,564 | 11/1993 | Matteucci | 536/23.1 |

OTHER PUBLICATIONS

Dempcy et al.(I), "Design and Synthesis of Deoxynucleic Guanidine: A Polycation Analogue of DNA," *Proc. Nat. Acad. Sci. USA*, 91, 7864–7868 (Aug. 1994).
Zon, "Oligonucleotide Analogues as Potential Chemotherapeutic Agents," *Pharmaceutical Research*, 5(9), 539–549 (1988).
Vanderdreissche et al.(I), "Synthesis, Enzymatic Stability and Base–Pairing Properties of Oligothymidylates Containing Thymidine Dimers with Different N–Substituted Guanidine Linkages," *J. Chem. Soc., Perkin Trans I*, 1993, 1567–1575.
Vanderdreissche et al.(II), "Synthesis of Novel N–Substituted Guanidine Linked Nucleoside Dimers and Their Incorporation into Oligonucleotides," *Bioorg. & Medicinal Chem. Letters,*, 3(2), 193–198(1993).
Dempcy et l.(II), "Synthesis of a Thymidyl Pentamer of Deoxyribonucleic Guidine and Binding Studies with DNA Homopolynucleotides," *Proc. Nat. Acad. Sci. USA*, 92, 6097–6101 (Jun. 1995).
Browne et al., "Binding Studies of Cationic Thymidyl Deoxyribonucleic Guanidine to RNA Homopolynucleotides," *Proc. Nat. Acad. Sci. USA*, 92, 7051–7055 (Jul. 1995).
Dempcy et al. (III), "Synthesis of the Polycation Thymidyl DNG, Its Fidelity in Binding Polyanionic DNA/RNA, and the Stability and Nature of the Hybrid Complex," *J. Am. Chem. Soc.*, 117(22), 6140–6141 (1995).
Theophilus et al., "Fundamental Principles and Diagnostic Applications of Molecular Biology," Ch. 1 in *Molecular and Antibody Probes in Diagnosis,* Walker and Rapley eds., John Wiley & Sons, New York, NY, 1993, pp. 3–39.

Gura, "Antisense Has Growing Pains—Efforts to Develop Antisense Compounds for Cancer, AIDS, and Other Diseases Have Encountered Some Unexpected Questions About How the Drugs Really Work," *Science*, 270, 575–577 (Oct. 27, 1995).
Krieg et al., "CpG Motifs in Bacterial DNA Trigger Direct B–Cell Activation," *Nature*, 374, 546–549 (Apr. 6, 1995).
Stein, C.A., and Cheng, Y.–C. (1993) Antisense Oligonucleotides as Therapeutic Agents—Is the Bullet Really Magical?, Science 261:1004 (Exhibit 4) (Aug.).
Almarsson, Orn and Bruice Thomas C. (1993) Peptide Nucleic Acid (PNA) Conformation and Polymorphism in PNA–DNA and PNA–RNA Hybrids, Proc. Nat. Acad. Sci. USA, 90:9542–9546 (Exhibit 5) (Oct.).
Agrawal, S., et al. (1991) Pharmacokinetics, Biodistribution, and Stability of Oligodeoxynucleotide Phosphorothioates in Mice, Proc. Natl. Acad. Sci. USA 88:7595 (Exhibit 6) (Sep.).
Fanton, E.; Gelas, J., and Horton D. (1980) Novel Modes for Selective Protection of Ketose Sugars and Oligosaccharides of Biological and Industrial Importance, J. C. S., Chem. Comm., (Exhibit 7), 21–22.
Maniatis, Sambrook, Fritsch, and Maniatis, (1989) Conditions of Hybridization of Oligonucleotide Probes, Molecular Cloning: A Laboratory Manual, p. 11.45–49, Cold Spring Harbor Press (Exhibit 8).
Vorbruggen, H.; Niedballa, U.; Krolikiewicz, K.; Bennua, B.; Hofle, G. (1978) On The Mechanism of Nucleoside Synthesis, Chemistry and Biology of Nucleosides and Nucleotides, Academic Press, Inc. p. 251–265 (Exhibit 9).
Vorbruggen, H.; Hofle G. (1981) On the Mechanism of Nucleoside Synthesis. Chem. Ber. 114:256–1268 (Exhibit 10).
Saneyoshi, M.; Fujii, T.; Kawaguchi, T.; Sawai, K.; Kimura, S. (1991) 3'–Amino–2'.3'–dideoxycytidine and 3'–amino–3' deoxythymidine. Their 5'–Triphosphates: An Improved Synthesis. Convenient Reduction of Azidonucleosides and Azidonucleotides by Hydrogen Sulfide, Nucleic Acid Chemistry, Section III: Nucleosides, New York, pp. 67–72 (Exhibit 11).
Horwitz, J. P.; Tomson, A. J.; Urbanski, J. A.; Chua, J. (Sep. 1962) Nucleosides. 5'–Amino–5'–deoxyuridine and 5'–Amino–5'deoxythymidine[1a,b], J. Org. Chem. 27:3045–3048 (Exhibit 12).
Brooks, B. R.; Bruccoleri,R. E.: Olafson, B. D.; States, D. J.; Swaminathan, S.; Karplus, M. (1983) CHARMM: A Program for Macromolecular Energy, Minimization, and Dynamics Calculations, J. Comput. Chem. 4:187–217 (Exhibit 13).

(List continued on next page.)

*Primary Examiner*—John Kight
*Assistant Examiner*—L. Eric Crane
*Attorney, Agent, or Firm*—Mandel & Adriano

[57] ABSTRACT

The invention provides a cationic polynucleoside chain having multiple nucleosides, the nucleosides being coupled together by positively charged guanidyl linkages.

6 Claims, 23 Drawing Sheets

OTHER PUBLICATIONS

Camerman, N.; Fawcett, J. K.; Camerman, A. (1976) Molecular Structure of a Deoxyribose–dinucleotide, Sodium Thymidylyl–(5'j 3')–Thymidylate–(5') Hydrate (pTpT), and a Possible Structural Model for Polythymidylate, J. Mol. Biol. 107:601–621 (Exhibit 14).

Luger, P.; Paulsen H. (1976) Röntgenstrukturanalyse von Tri–O–acetyl–β–D–xylopyranosylazid zur Untersuchung des Exoanomeren Effekts der Azidogruppe, Acta Cryst B32:2774–2779 (Exhibit 15).

Almarsson, Ö.; Bruice, T. C.; Kerr, J.; Zuckermann, R. N. (Aug. 1993) Molecular Mechanics Calculations of the Structures of Polyamide Nucleic Acid DNA Duplexes and Triple Helical Hybrids, Proc. Natl. Acad. Sci. USA, 90:7518–7522 (Exhibit 16).

Raghunathan, G.; Miles, H. T.; Sasisekharan, V. (1993) Symmetry and Molecular Structure of a DNA Triple Helix: d(T)η.d(A)ηld(T)η, Biochemistry 32:455–462 (Exhibit 17) (Issue No. 2).

Glinski,r. P.; Khan, M. S.; Kalamas, R. L. (1973) Nucleotide Synthesis, IV. Phosphorylated 3'–Amino3'–deoxythymidine and 5'–Amino–5'–deoxythymidine and Derivatives, J. Org. Chem. 38(25):4299–4305 (Exhibit 18) (Issue No. 25).

Buschauer, A. (1989) Synthesis and in Vitro Pharmacology of Arpromidine and Related Phenyl(pyridylalkyl)guanidines, a Potential New Class of Positive Inotropic Drugs, J. Med. Chem., 32:1963–1970 (Exhibit 19) (Issue No. 8).

a) Proposed synthetic step.

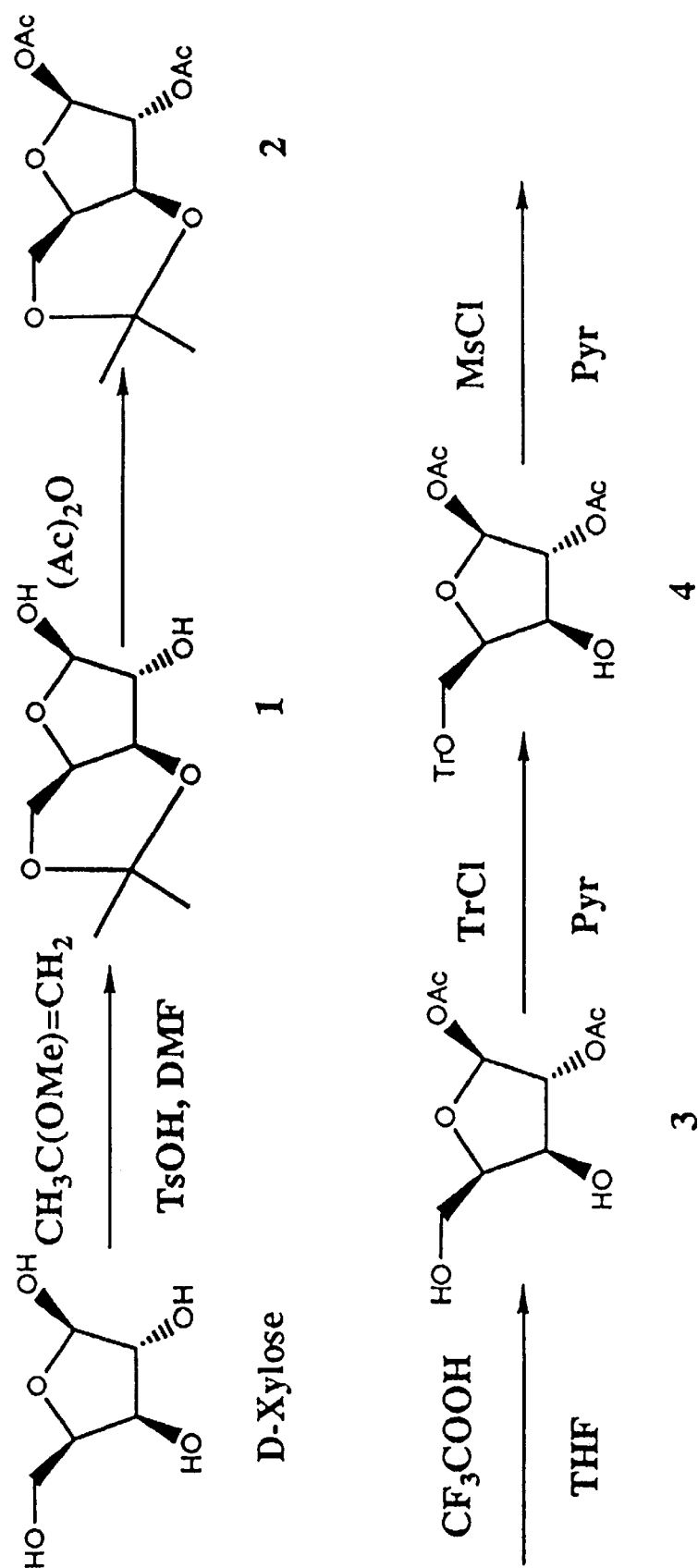
FIG. 4A  Synthesis of 5'-OH Terminal Unit of RNG

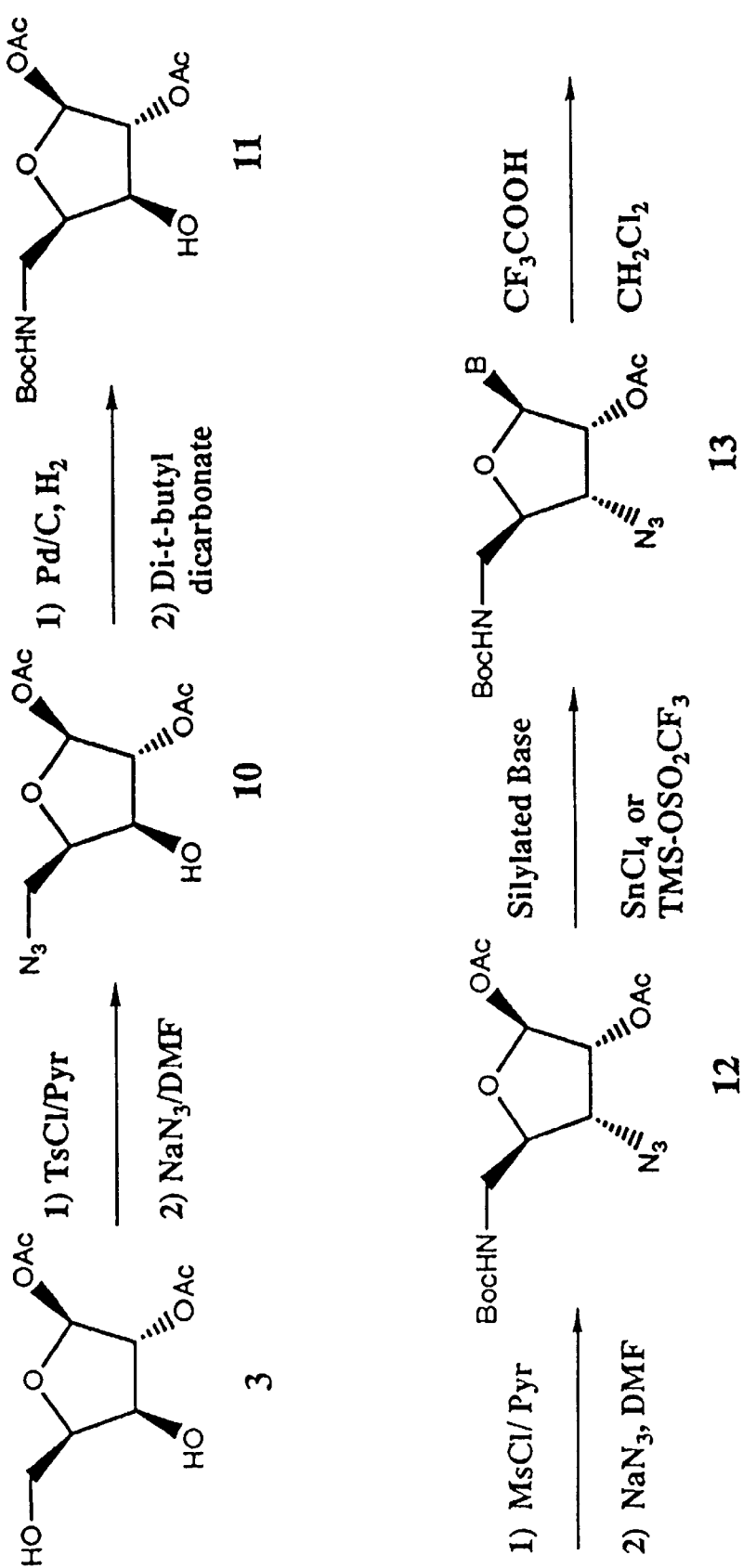
FIG. 5A  Synthesis of Chain-Extending Unit of RNG

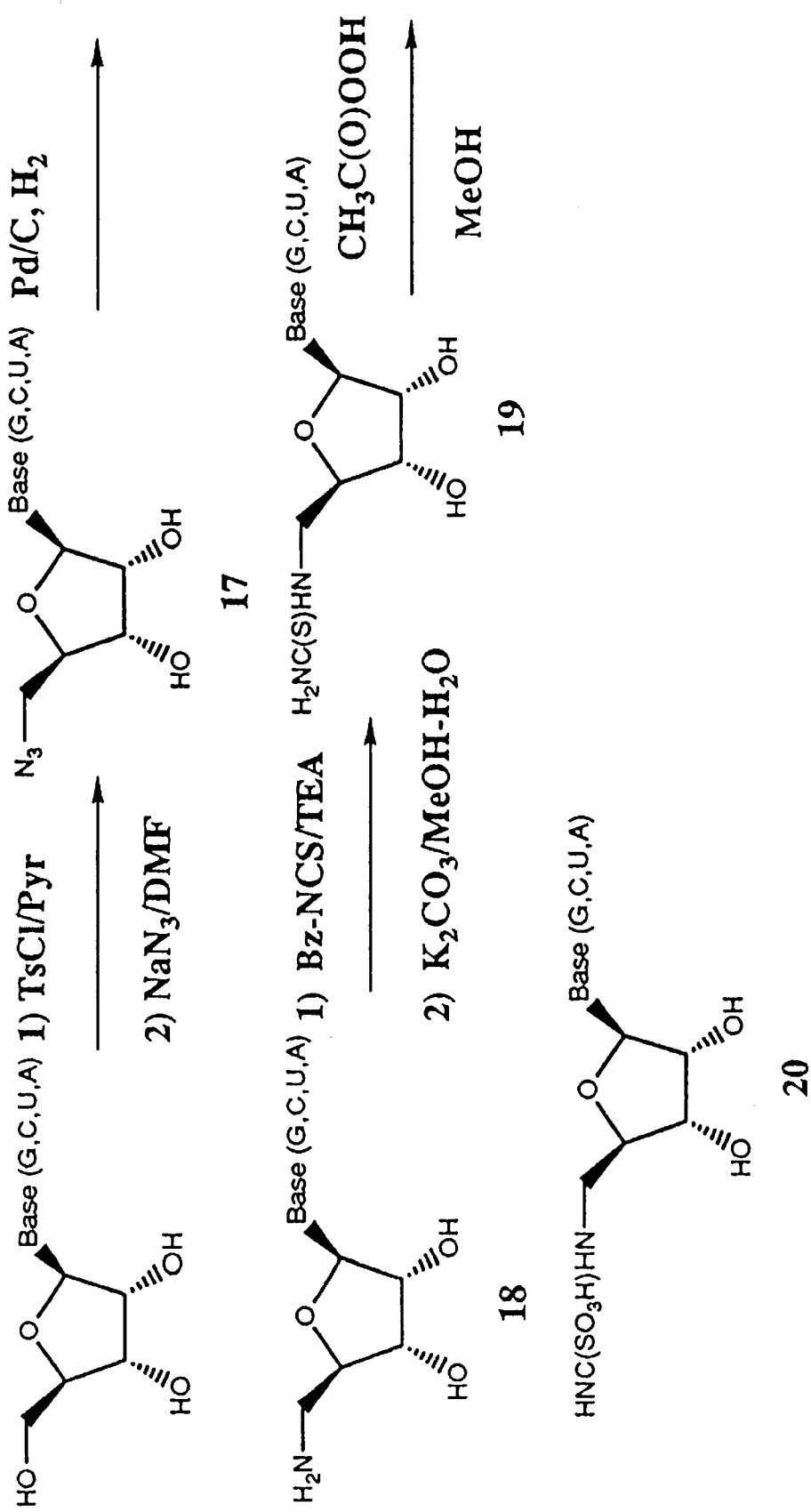
FIG. 6 Synthesis of 3'-OH Terminal Unit of RNG

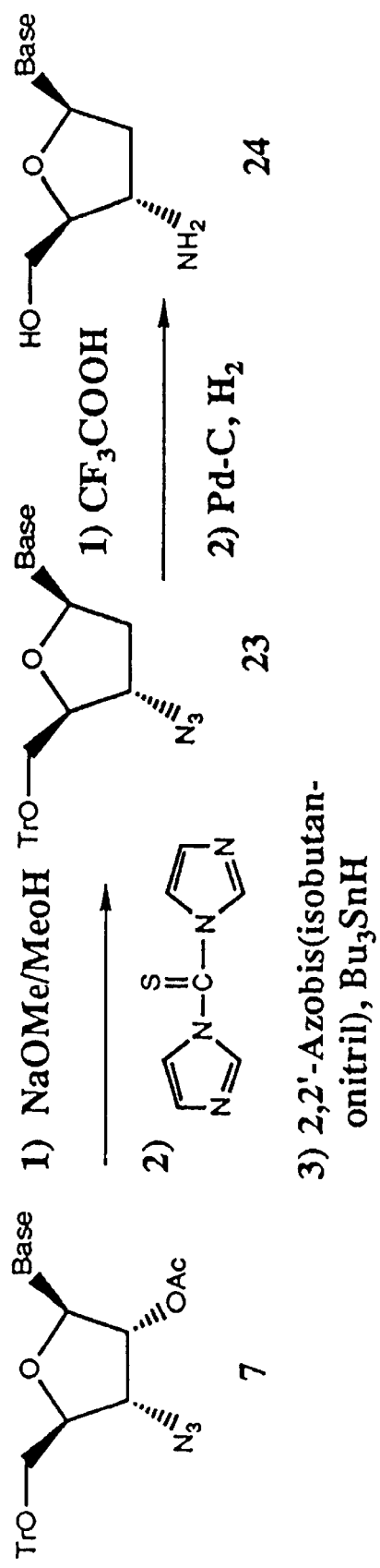
FIG. 7  Synthesis of 5'-OH Terminal Unit of DNG

FIG. 8 *Synthesis of Chain-Extending Unit of DNG*
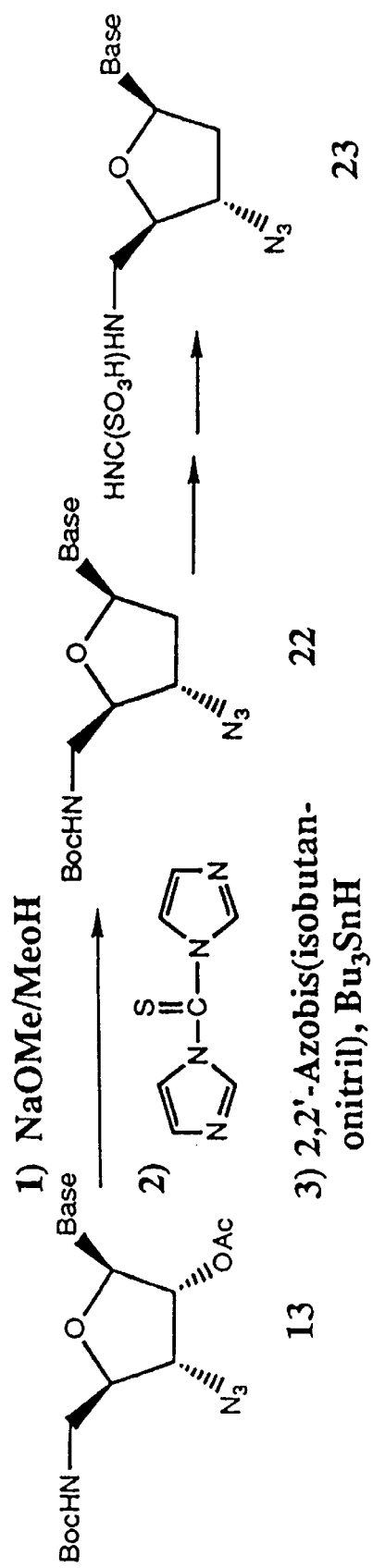

Synthesis of 3-OH Terminal Unit of DNG

FIG. 10
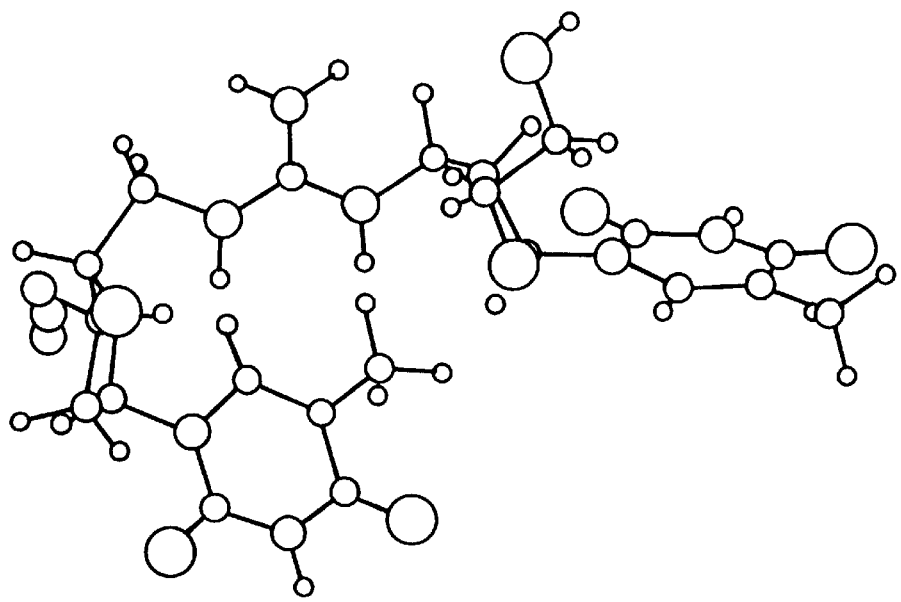
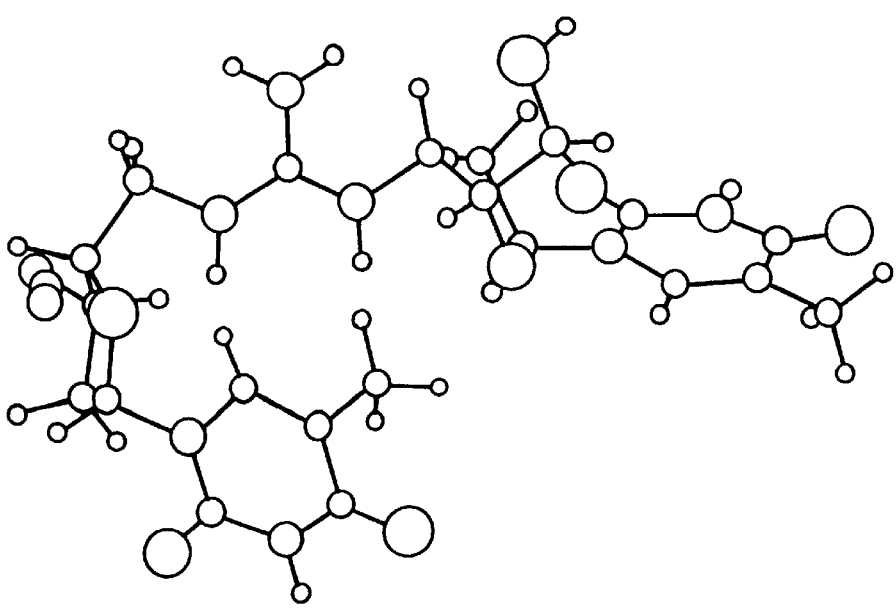

FIG. 16
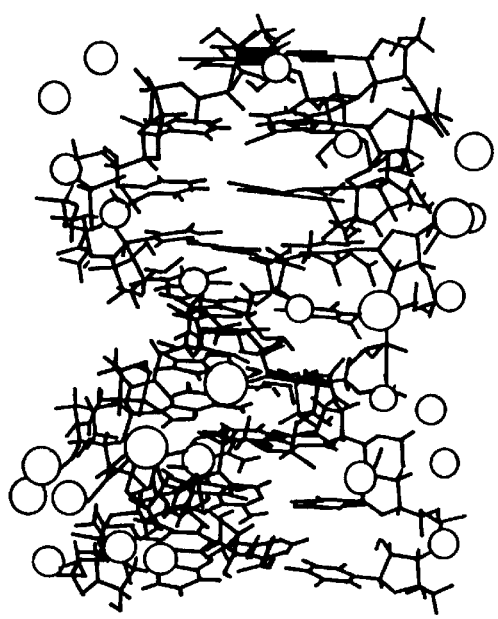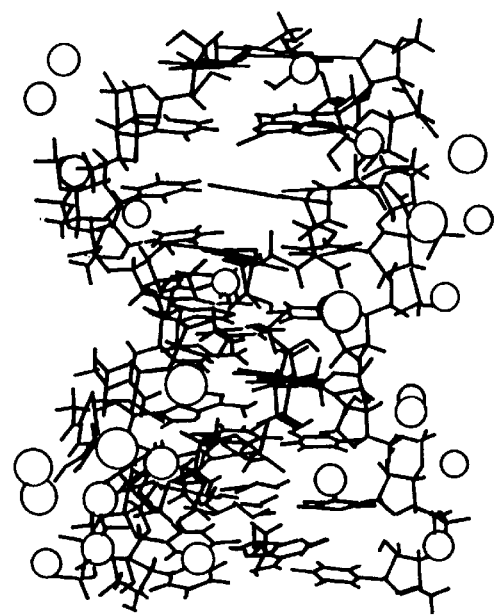

POLYNUCLEOSIDE CHAIN HAVING MULTIPLE RIBONUCLEOSIDES, THE NUCLEOSIDES COUPLED BY GUANIDYL LINKAGES

This application is a continuation-in-part of U.S. Ser. No. 08/268,859, filed Jun. 30, 1994, now U.S. Pat. No. 5,696,253 the contents of which are incorporated by reference into the present application.

ACKNOWLEDGEMENT OF GOVERNMENT SUPPORT

This invention was made with Government support under Grant Contract No. NOOO14-90-J-4132 awarded by the Office of Naval Research and Grant No. DMB 9002173 awarded by the National Science Foundation. The Government has certain rights in this invention.

BACKGROUND OF THE INVENTION

Oligonucleotide technology utilizes short sequences of nucleic acids as highly specific probes to assay the presence of DNA and/or RNA sequences of interest. It also has applications for treating diseases as it can be used to selectively inhibit the expression of genes of interest. As such, oligonucleotide technology has great potential in the analysis and treatment of genetic disorders.

As an example, genetic disorders account for approximately 30 percent of admissions to pediatric hospitals. Therefore, the ability to provide a comprehensive diagnostic molecular genetic service is an important aspect of a modern health care system.

In order to solve problems attendant in some applications using oligonucleotides, such as degradation by host cell nucleases, or transfer across cell membranes, oligonucleotide analogs have been constructed by replacing a non-bridging oxygen in the phosphate moiety with a sulfur, methyl or ethyl group (reviewed in Stein, C. A., and Cheng, Y.-C., *Science* (1993) 261: 1004). A second example of an oligonucleotide analog is one using a formacetal/ketal type linkage replacing one or more phosphodiester linkages between adjacent nucleosides. (U.S. Pat. No. 5,264,564, issued Nov. 23, 1993).

Dimeric nucleosides have also been constructed with uncharged guanidyl linkages replacing some phosphodiester bonds. Vandendriessche et al. provide a method for synthesizing thymidine nucleosides coupled together with substituted guanidyl linkages, J. Chem. Soc. Trans. 1: 1567 (1993); Bioorg. Med. Chem. Lttrs. 3(2): 193–198 (1993). The electron-withdrawing properties of the substituent groups make the guanidyl moiety uncharged at physiological Ph. These thymidine dimers can be incorporated into oligonucleotide chains with standard phosphate backbones.

Vandendriessche et al. developed their method using neutral guanidyl groups for coupling nucleosides because they reasoned that positively charged groups may hamper cellular uptake of oligonucleosides containing them and may lead to non-specific binding.

However, the resulting method having uncharged guanidyl units at physiological pH is limited in its applications to oligonucleoside technology. It does not allow for construction of oligonucleoside chains containing two or more successive guanidyl linkages. Instead, each nucleoside connected to one nucleoside via a guanidyl linkage must be attached to a second with a phosphodiester linkage. Thus, many of the advantages provided by guanidyl linkages are undermined.

For example, the necessity for phosphodiester bonds following guanidyl bonds exposes oligonucleosides to cellular nucleases that recognize phosphodiester bonds.

A second limitation of the Vandendriessche method is that the electrically neutral guanidyl bridges will not interact with the phosphates on the backbones of naturally occurring nucleic acids.

The present invention overcomes both of these shortcomings. First, it provides an alternative approach to constructing oligonucleosides that utilizes guanidyl linkages having a positive charge at physiological pH. In addition, the method provides a way to construct a oligonucleoside chain built with successive positively charged guanidyl linkages. It is thus possible to use the present invention to construct a positively charged oligonucleoside chain that will bind with high affinity to negatively charged phosphate backbone of cellular and viral DNA or RNA.

The higher affinity binding reduces the incidence of false positives and facilitates earlier detection of a diseased state. Early detection of disease improves the patient's prognosis and aids in determining an optimal therapy regimen. Therefore, the diagnostic agents of the invention provide a means to determine disease states early, efficiently and predictably.

SUMMARY OF THE INVENTION

The present invention provides a polynucleoside chain having multiple nucleosides coupled together by positively charged guanidyl linkages. Assays for using such polynucleoside chains are also provided.

BRIEF DESCRIPTION OF THE FIGURES

FIGS. 4A, 4B and 4C. Protocol for synthesis of 5'-OH terminal unit of RNG.

FIGS. 5A and 5B. Protocol for synthesis of chain-extending units of RNG.

FIG. 6. Protocol for synthesis of 3'-OH terminal unit of RNG.

FIG. 7. Protocol for synthesis of 5'-OH terminal unit of DNG.

FIG. 8. Protocol for synthesis of chain-extending unit of DNG.

FIG. 10. Stereo view of a ball and stick model of 3'-Deoxythymidylyl-[3'-5'guanidyl]-3'-azido-3',5'-deoxythymidine Iodide generated from the X-Ray coordinates of thymidylyl-(5'3')-thymidylate-(5') hydrate.

FIG. 16. Stereo view of the triplex structure of (Up)$_9$U·r(A$_g$)$_9$A·(Up)$_9$U with counterions. The minor groove can be viewed from the upper left of the figure, where the Watson-Crick paired RNG strand and the RNA strand situate at the right and the left respectively. The major groove is at the lower right and the Hoogsteen strand RNA runs parallel with the RNG strand in the major groove.

DETAILED DESCRIPTION OF THE INVENTION

Figure 1A:
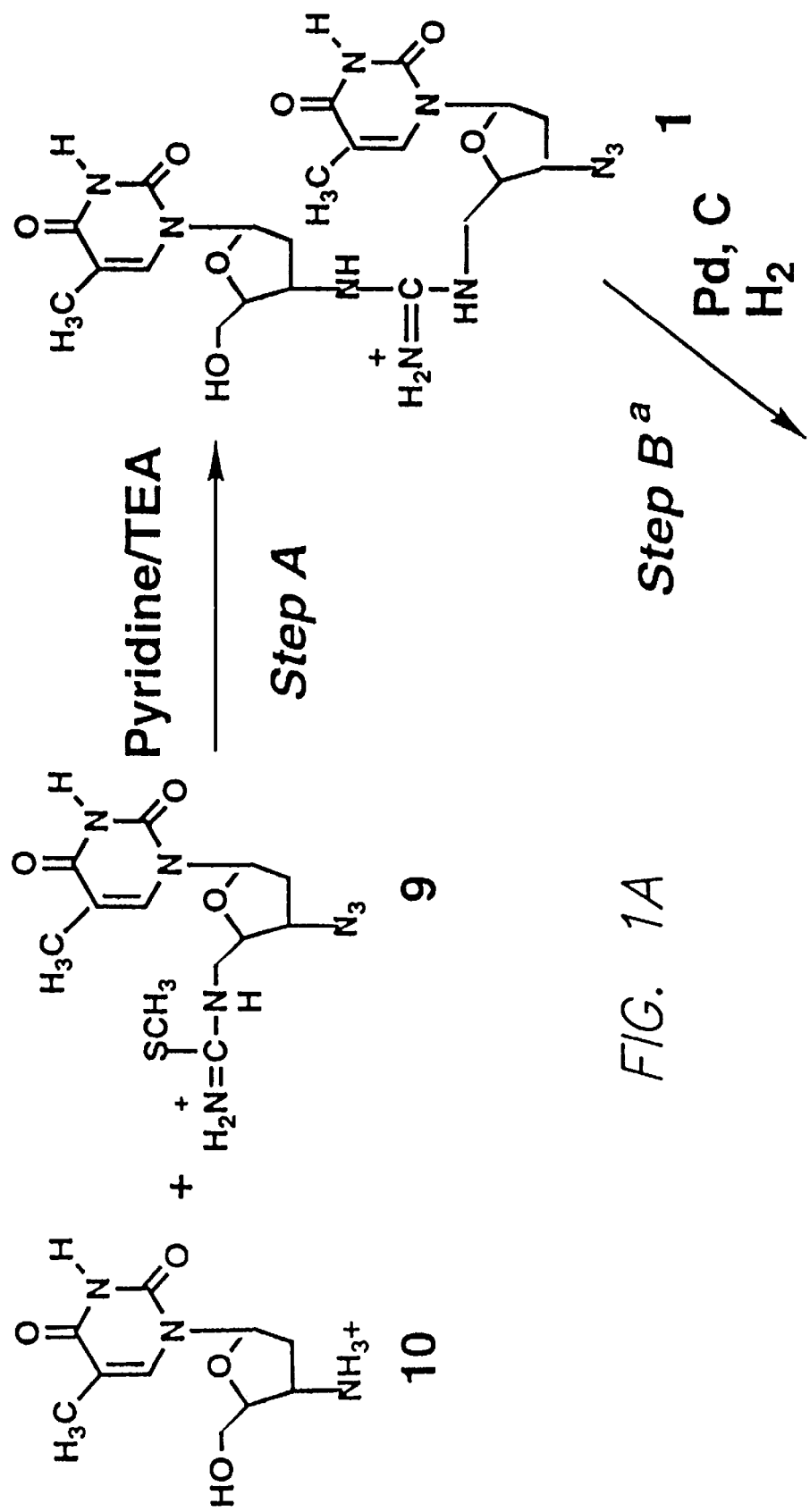
FIGS. 1A and 1B. The general synthetic strategy for the formation of thymidyl DNG oligomers.

The present invention provides a polynucleoside chain having multiple nucleosides. Each of the nucleosides in the chain are coupled together by positively charged guanidyl linkages.

Each nucleoside in the chain is made up of a sugar component and a purine or pyrimidine base. The sugar is 2'-deoxyribose for DNG and ribose for RNG. The base may be a guanine (G), cytosine (C), adenine (A), or thymine (T) in the case of DNG, or uracil (U) in the case of RNG. Each sugar component of the chain is linked to a purine or pyrimidine base at the C1' position of the sugar component. Each nucleoside of the chain is connected to another at the C5' and C3' positions of the sugar component by a positively charged guanidyl linkage replacing a phosphodiester linkage or other linkages.

The guanidyl linkage has the following formula:

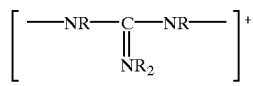

The R group represents a hydrogen molecule or a lower alkyl or phenyl group that does not alter the positive charge on guanidine. Examples of suitable lower alkyl groups include, but are not limited to, CH$_3$, CH$_2$CH$_3$, CH$_3$(CH$_2$)$_n$CH$_3$, CH$_2$X, CH$_3$CH$_2$X, CH$_3$(CH$_2$)$_n$CH$_2$X, wherein X is any functional group that does not alter the positive charge on guanidine. Examples include, but are not limited to, —OH or —NH$_2$.

The polynucleoside backbone of the invention may be composed entirely of guanidyl linkages, in which case the backbone is said to be homomeric with respect to guanidyl linkages, thereby resulting in homomers of the invention. Alternatively, some sugar components within one nucleoside chain are linked to one another through guanidyl linkages, and others are linked through a phosphate moiety. In this situation the polymer is said to be heteromeric, thereby resulting in heteromers of the invention. A description of how to synthesize homomers and heteromers of the invention is given in Example 1 and further herein.

For assembling an oligonucleoside chain, monoucleosides may be appended to the 5' and/or 3' end of the nucleosides of a homomer or heteromer. Alternatively, the mononucleosides may be inserted within the nucleosides of the homomer or heteromer.

In accordance with the practice of the invention, the polynucleoside chain may be a DNG chain which is substantially complementary to a gene sequence of interest. Alternatively, the polynucleoside chain may be a RNG chain which is substantially complementary to a gene sequence of interest. The polynucleoside may additionally be a chimera of RNG and DNG subunits.

The gene sequence of interest may be the DNA of any known sequence, a known genomic RNA such as an RNA virus or viroid, or an RNA transcribed from a DNA sequence of interest.

For example, the gene sequence of interest may be a segment of the nucleotide sequence of HTLV-I (U.S. Pat. No. 4,999,421, issued Mar. 12, 1991). Probes of the invention may be made and used for detecting HTLV-I DNA or RNA in samples suspected of being infected with HTLV-I.

In another example, the gene sequence of interest may be the nucleotide sequence of pregnancy-specific beta-glycoprotein (PSβG) cDNA that corresponds to a mRNA that is expressed at high levels in certain gestational diseases (U.S. Pat. No. 5,141,849, issued Aug. 25, 1992). Probes of the invention may be used for detecting Psβg RNA sequences in a sample of placental tissue.

In one embodiment, the polynucleoside chain of the invention is a component in a composition comprising an effective amount of the polynucleoside and a suitable pharmaceutical carrier. Suitable pharmaceutical carriers include water, saline, Ringer's solution, Hank's solution or nonaqueous carriers such as fixed oils. The carrier may also contain substances that enhance isotonicity and chemical stability of the chain such as buffers or preservatives.

The compositions of the invention also preferably include conventional pharmaceutically acceptable carriers and adjuvants known in the art such as human or bovine serum albumin, ion exchangers, alumina, lecithin, buffer substances such as phosphates, glycine, sorbic acid, potassium sorbate, and salts or electrolytes such as protamine sulfate.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. Examples of ionic detergent includes, but are not limited to, alkyltrimethylammonium bromide and sodium dodecyl sulfate.

Additionally, in accordance with the invention, the lipid carrier may be a liposome. As used in this application, a "liposome" is any membrane bound vesicle which contains any molecules of the invention or combinations thereof.

USES OF THE PRESENT INVENTION

The oligonucleosides of the invention may be used to identify specific nucleic acids either as probes in nucleic hybridization assays, or via amplification techniques such as the polymerase chain reaction (PCR). Because the identification of specific DNA and/or RNA sequences is often indicative of a disease state, the ability to detect specific nucleic acids with the invention has both diagnostic and prognostic value.

The molecules of the invention may be used in various assays utilizing antibodies raised against them. These anti-DNG or anti-RNG antibodies can then be used in assays such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLIFA) and the like. The assays may be homogeneous (without a separation step between free reagent and receptor-ligand complex) or heterogeneous (with a separation step between free reagent and receptor-ligand complex).

The reagents may be supplied in a kit, so as to facilitate ease of application of the invention and also to optimize the invention's reproducibility and sensitivity.

For the subject invention, depending upon the nature of the assay, the protocol, and the label, either labeled or unlabeled polynucleoside chain is provided, usually in conjunction with other additives, such as buffer, stabilizers, materials necessary for signal production, e.g., substrates for enzymes, and the like.

DNG and RNG oligonucleosides containing guanidyl linkages will be labeled by DNA modification enzymes routinely used to label nucleic acids. Because the invention allows the addition of nucleosides via either guanidyl or phosphate linkages, it is possible to construct chains with conventional phosphate linkages at the extreme 5' or 3' termini.

A DNG or RNG oligonucleoside can be radiolabeled by kinasing its 5'end with gamma-$^{32}$P ATP and T4 polynucleotide kinase. Alternatively, DNG oligonucleosides can be radiolabeled using terminal deoxynucleotidyl transferase and alpha-$^{32}$P-dNTP.

The oligonucleosides can also be labeled using non-radioactive labeling methods. For example, a DNG oligonucleoside can be labeled by using terminal transferase to add digoxigenin-11-dUTP to its 3' end using a method for labeling oligonucleotides developed by Bohringer-Mannheim Corporation, Indianapolis, Ind.

Following hybridization, the probe can be detected with an antibody specific for the digoxigenin moiety. The antibody is conjugated to an easily detectable reporter molecule such as alkaline phosphatase.

Depending on the particular application, an oligonucleoside probe should have at least about 14 nucleosides and may range upward in size to over one hundred nucleosides.

The reagents are provided as a dry powder, where the reagents may be reconstituted in an aqueous medium having appropriate concentrations for performing the assay. Alternatively, the reagents are in a liquid medium.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the location of the disease being treated, the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. Cancer Chemother., Rep. 50 (4): 219–244 (1966). An approximation of the in vivo dosage of oligonucleotides is about 30 mg/kg of body weight, Agrawal, S. et al. Proc. Natl. Acad. Sci. USA 88 (17): 7595. Adjustments in the dosage regimen may be made to optimize the tumor cell growth inhibition and killing, e.g., doses may be divided and administered on a daily basis or the dose reduced proportionally depending upon the situation, e.g. several divided doses may be administered daily or proportionally reduced.

It would be clear that the dose of the composition of the invention required to achieve cures may be further reduced with schedule optimization.

The use of probes to bind the target may be carried out in any conventional techniques such as nucleic acid hybridization, plus and minus screening to identify sequences differentially expressed in different RNA populations, recombinational probing, hybrid released translation (HRT), hybrid arrested translation (HAT), and amplification techniques such as polymerase chain reaction (PCR). Probes constructed by the invention may also be used to detect proteins that bind to specific nucleic acid sequences.

The present invention additionally provides a method for inhibiting the expression of a cellular gene. The method comprises constructing a DNG or RNG oligonucleoside with a sequence complementary to a portion of the known sequence of a transcribed sequence of interest; delivering said oligonucleoside to the target tissue; contacting said oligonucleoside with the transcribed sequence of interest; forming a complex between the said oligonucleoside and the transcribed sequence; and the complex then capable of preventing or inhibiting proper folding of the transcribed sequence or translation of the transcribed sequence.

The present method further provides a method for inhibiting the replication of a virus. The method comprises contacting the nucleic acid comprising the genome of the virus with the polynucleoside of the invention thereby permitting the formation of a double-stranded complex. The complex obstructs replication transcription, and translation of the viral genome. Production of progeny viral particles is thereby prevented.

The present invention also provides a method for inhibiting viral replication by preventing viral integration into the genome of a host cell. The method comprises determining the presence of a virus by detecting the presence of a viral nucleic acid sequence; constructing a polynucleoside of the invention which is substantially complementary to at least a portion of the viral sequence required for integration in to the host cell genome; and contacting the polynucleoside of the invention with the viral sequence so as to form a nucleoside-viral sequence complex, the complex so formed capable of preventing viral integration into the genome of the host cell.

Methods of Making Polynucleoside Chains of the Present Invention

Figure 3A:
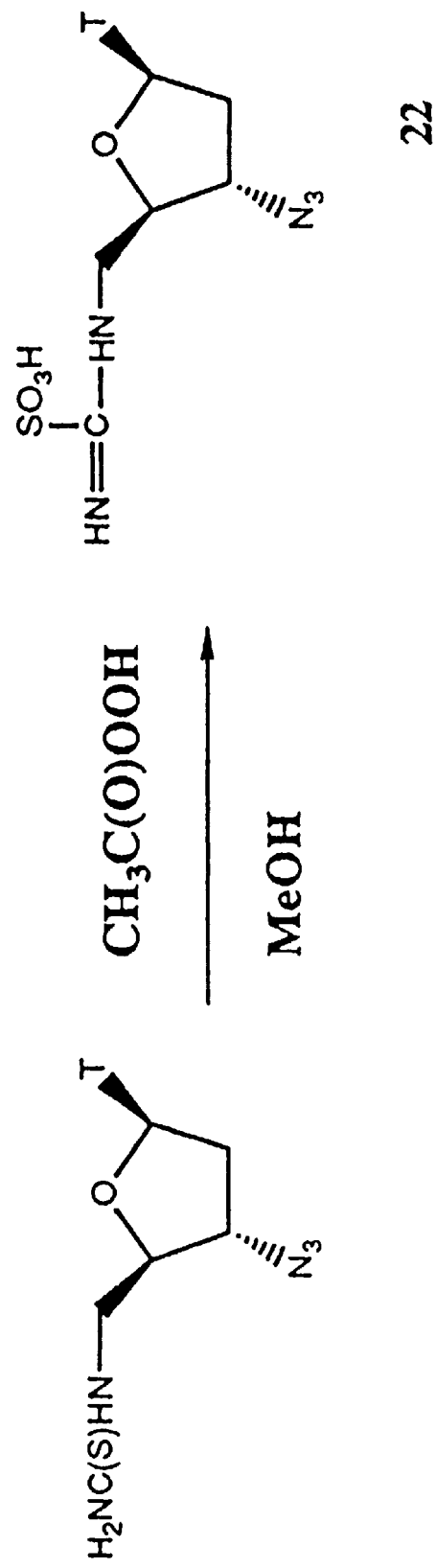
FIGS. 3A and 3B. DNG coupling reaction.
Figure 3B:
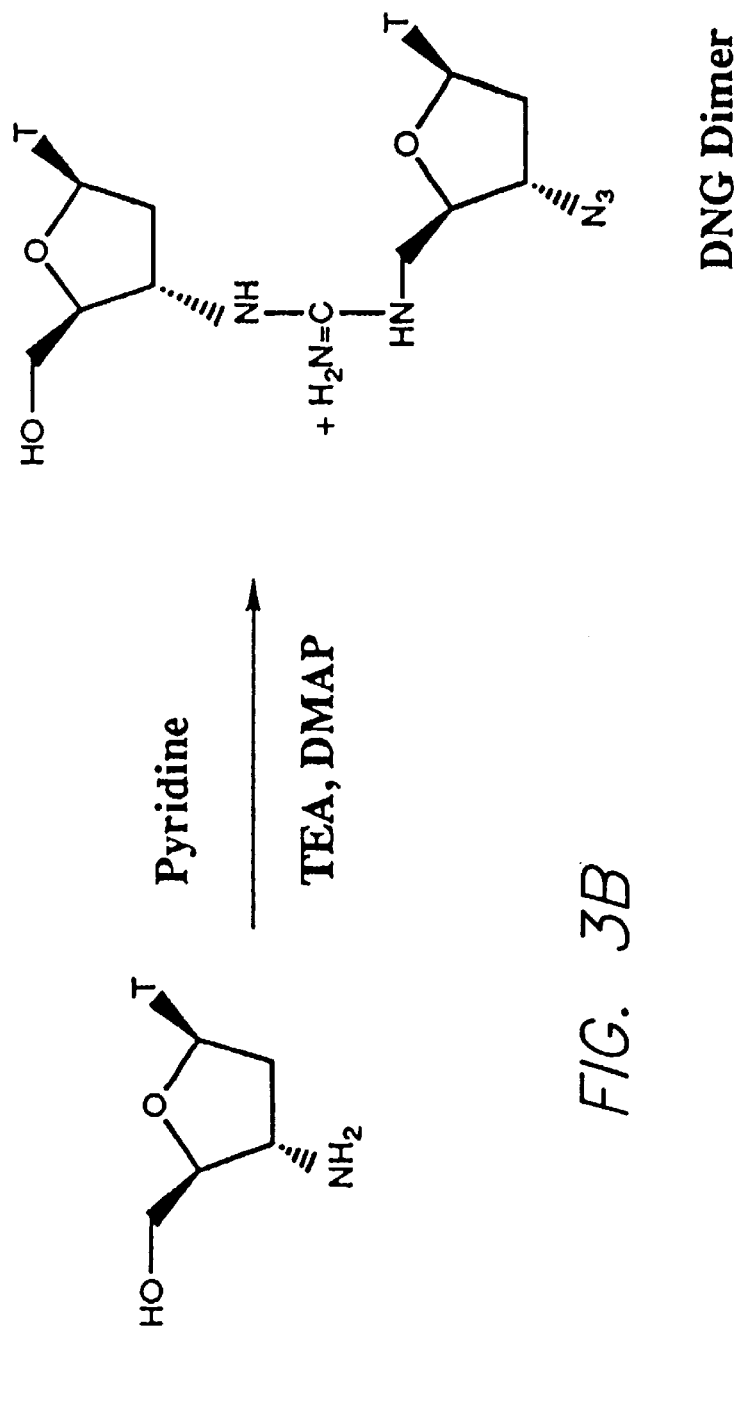

The following synthetic methodology results in the formation of the 3',5'-guanidyl linkage of the polynucleosides of the invention. Oxidation of 3'-azido-5'-thiourea-3',5'-deoxythymidine with peracetic acid in methanol (FIGS. 3A and 3B) provided the 5'-aminoiminomethanesulfonic acid derivative 22 which proved superior as an intermediate (faster reaction time) in the DNG coupling reaction in place of 3'-azido-5'-S-methylisothiouronium-3',5'-deoxythimidine Iodide. Thus the reaction of 22 with 3'-amino-2',3'-deoxythymidine in the presence of 4-dimethylaminopyridine (DMAP) produces the thymidine DNG dimer in yields greater than 90%.

Figure 4B:
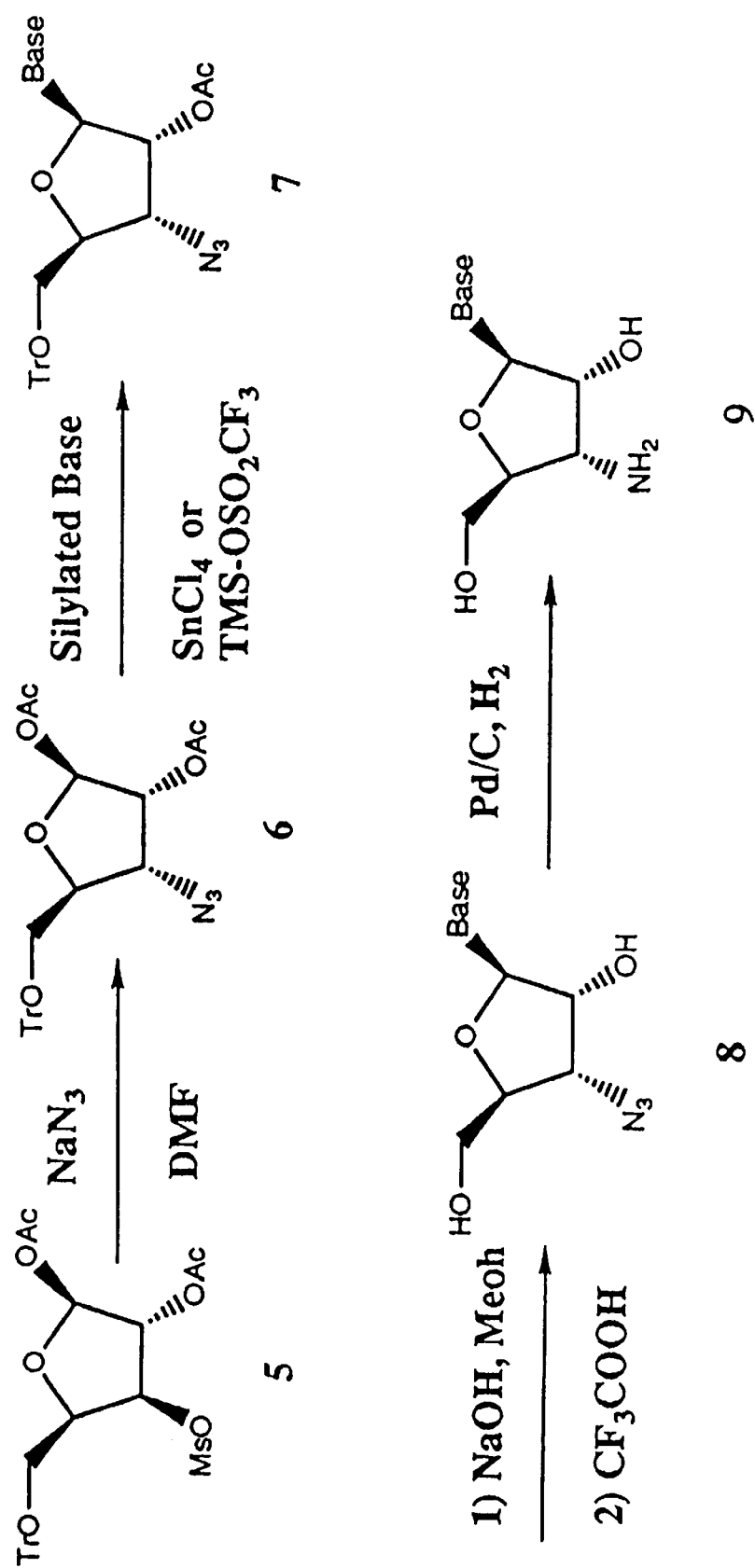
Figure 4C:
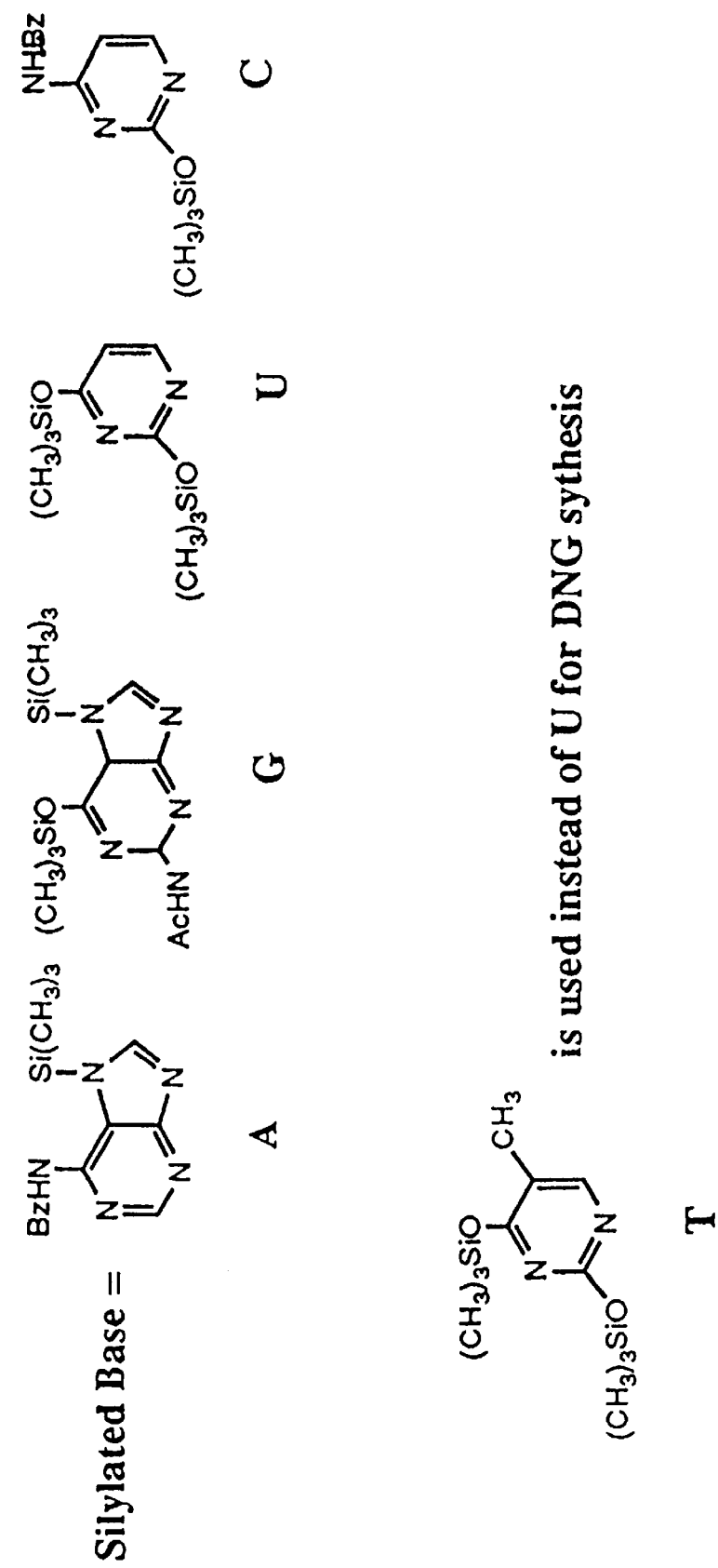

General synthetic methodology for the formation of RNG (ribonucleic guanidine) is illustrated in FIGS. 4A–6. Synthesis of the 5'-terminal unit of RNG is shown in FIGS. 4A, 4B and 4C. The reaction of D-xylose with 2-methoxypropene results in the selective formation of the 1,3-O-isopropylidene product 1 (Fanton E.; Gelas, J.; Horton, D., *J. Chem. Soc., Chem. Commun.,* (1980), 21). Acetylation of the 1- and 2-hydroxyl's with acetic anhydride followed by cleavage of the isopropylidene moiety with trifluoracetic acid provides intermediate 3. Selective 5-protection is accomplished by reaction of 3 with trityl chloride in pyridine. Functionalization of the 3-position as the azide moiety involves two steps starting with the mesylation of 4 followed by nucleophilic substitution with sodium azide. The acetate moieties protecting the 1- and 2-positions of 5 are reportedly stable in the presence of azide ion (Greene, T. W.; Wuts, P. G.; In *Protecting Groups in Organic Synthesis,* Wiley-Interscience Publication: New York (1991); p. 418).

Compound 6, now containing the ribose ring configuration, can be alkylated at the C-1' position (with beta stereochemistry) utilizing standard Vorbruggen reaction conditions (Vorbruggen, H.: Nieballa, V.; Krolikiewicz, K.; Bennua, B.; Hofle, G. In *Chemistry and Biology of Nucleosides and Nucleotides,* Harmon, R. E., Robins, R. K., Townsend, L. B., Eds.; Academic Press: New York (1978); p. 251; Vorbruggen, H.; Hofle, G., *Chem. Ber.* (1981), 114, 1256).

Any of the natural RNA or DNA bases can be applied to this reaction. The resulting nucleoside 7 is deprotected with sodium methoxide followed by trifluoroacetic acid. The 3'-azido nucleoside 8 is then converted to the amino analogue by catalytic hydrogenation, producing the 5'-OH coupling intermediate 9.

Chain extension of the RNG polynucleoside of the invention is as follows. The chain-extending RNG intermediate 15 (FIGS. 5A and 5B) begins with the conversion of 3 to the 5-azido analogue 10 by a two-step process involving tosylation followed by nucleophilic substitution. Compound 10 is then reduced to the resulting amine and protected with the t-butyl carbamate protecting group. After mesylation, 11 is converted to the 3'-azido compound 12 by treatment with sodium azide. Conversion of 12 to the desired nucleoside is followed by deprotection of the 5'-amino group with trifluoroacetic acid. Compound 14 is converted to the sulfonic acid derivative 16 by a three-step process involving formation of the 5'-thiourea followed by oxidation of the sulfur atom with peracetic acid.

FIG. 6 illustrates the synthesis of the 3'-OH terminal coupling unit of RNG. Any of the natural nucleosides are easily converted to the 5'-azido derivatives by selective 5'-tosylation followed by nucleophilic substitution. Catalytic reduction is followed by conversion of the resulting amine to the thiourea analogue 19. Oxidation of 19 to the sulfonic acid coupling intermediate 20 is accomplished with peracetic acid in methanol.

This discovery includes the synthesis of oligomeric RNG. The RNG building blocks were prepared by stereoselective ribosylation of presilylated $N^6$-benzoyl adenine with the 1,2-diacyl intermediate 10 (Scheme 4) under standard Vorbruggen reaction conditions (treatment of 10 (Scheme 4) with the lewis acid trimethylsilyl triflate affords a resonance stabilized ribofuranosyl carbocation which alkylates at the b-position of C-1). This methodology may be extended to the synthesis of RNG building blocks incorporating any of the other natural nucleobases (U, G and C) and is currently being utilized in the preparation of RNG oligomers with mixed nucleobase sequences.

The methodology described above allows for the synthesis of RNG homomers, or by incorporation of a 3'- or 5'-hydroxyl group, the synthesis of RNG heteromers (RNG with RNA units interspersed throughout the polymer backbone).

The general synthesis for DNG homomers or heteromers is similar to that described for RNG polymers. However, DNG oligomer synthesis includes a chemical step resulting in the dehydroxylation at the 2'-position. For example, synthesis of the 5'-OH terminal unit of DNG (FIG. 7) utilizes intermediate 7. Deacetylation is followed by conversion of the 2'-OH group to the thiocarbonyl ester which is reduced to the 2'-deoxynucleoside 23 with tributyltin hydride (Singh, J.; Wise, D.; Townsend, L. In *Nucleic Acid Chemistry,* Part 4. Townsend, L. B., Tipson, R. S., Eds; Wiley-Interscience Publication: New York (1991); p. 96). Deprotection of the 5'-position with trifluoroacetic acid followed by reduction of the azide moiety to the amine by catalytic hydrogenation provides the coupling intermediate 24.

Figure 5B:
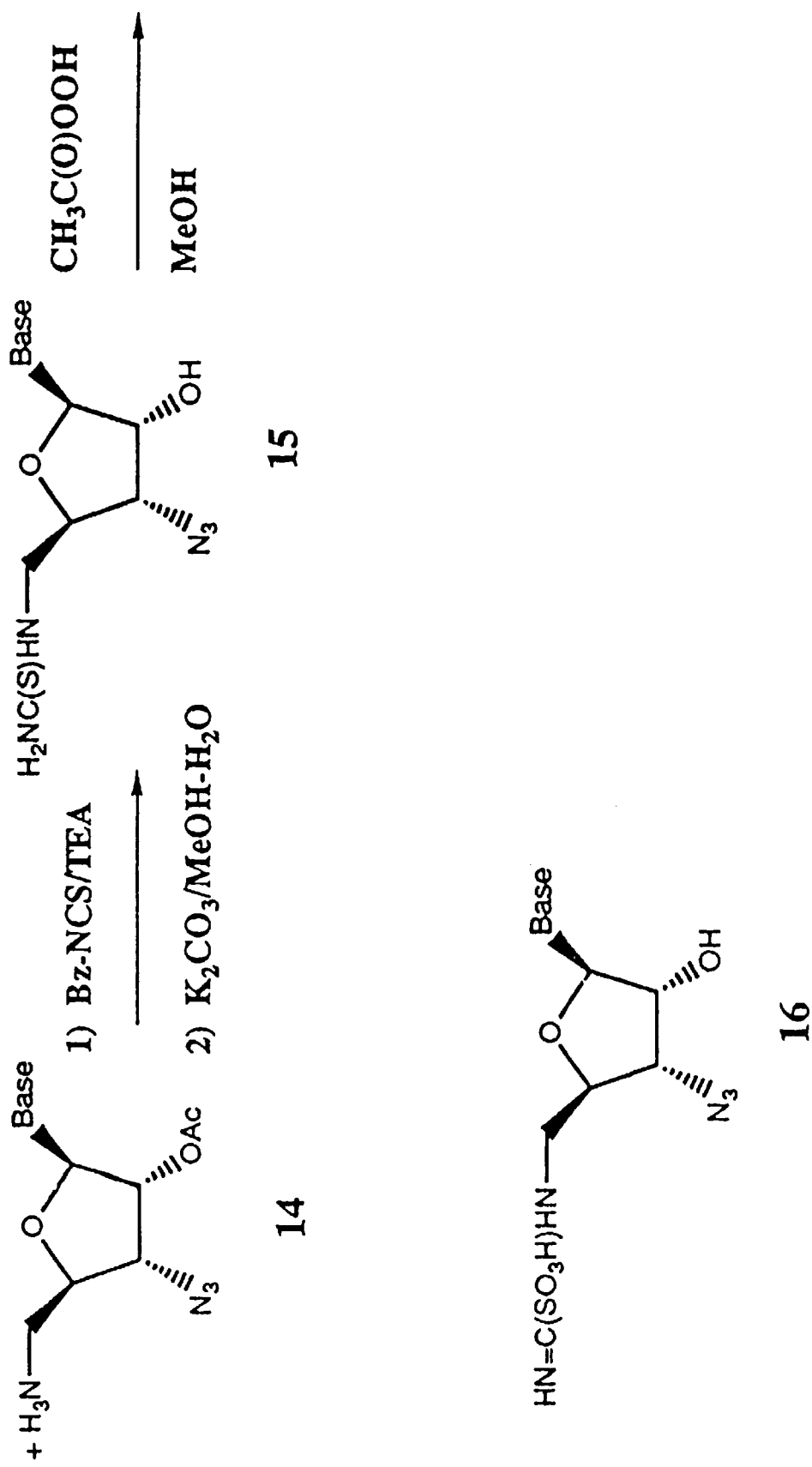

Chain extension of the DNG polynucleoside of the invention is as follows. FIG. 8 sets forth the synthesis of the chain-extending unit of DNG. Thus, intermediate 13 is converted to compound 22 which then converted into the coupling intermediate 23 by the same sequence of reactions used for the synthesis of 16 for 13 (FIGS. 5A and 5B).

Figure 9:
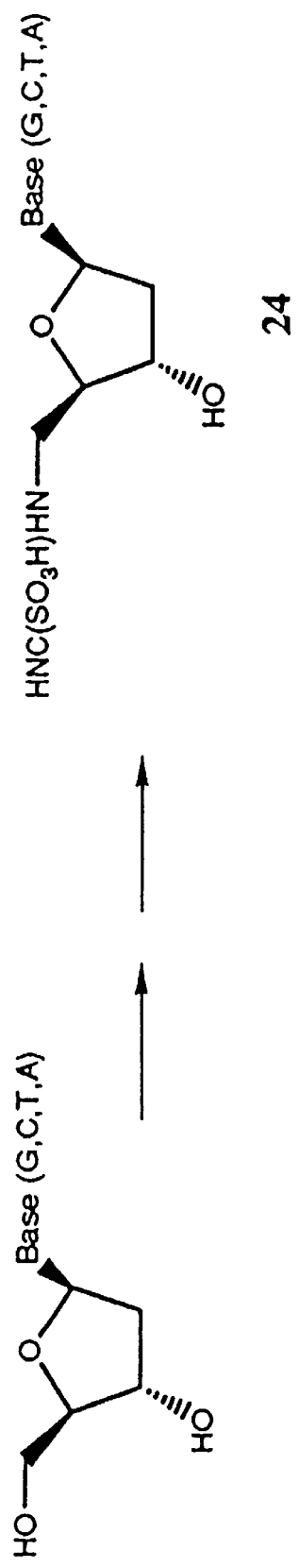
FIG. 9. Protocol for synthesis of 3'OH terminal unit of DNG.

The synthesis of the 3-OH terminal unit of DNG (FIG. 9) starts with any of the natural DNA nucleosides. The 5'-position is functionalized to the sulfonic acid derivative by a similar set of reactions as depicted in FIGS. 5A and 5B.

The synthetic methodology described above allows for the synthesis of DNG or RNG homomers or heteromers of the invention capable of targeting any gene or RNA sequence of interest.

Advantages of the Present Invention

Applicants' discovery involves replacing the phosphate linkage of DNA with a guanidyl linkage which imparts a cationic charge to the molecule. The advantage obtained by such a replacement is that the positively charged guanidyl linkages will interact electrostatically with the negatively charged phosphate linkages of target nucleic acids, thus providing electrostatic stabilization of DNG-DNA and DNG-RNA double and triple helical complexes.

The oligonucleosides of the present invention are stable. In the past, significant effort has been expended by chemists to develop nuclease-resistant oligonucleotides. Perhaps the greatest successes in doing so have been achieved with the phosphorothioate (PS) and methylphosphoroate (MP) oligos. Because nucleosides of the present invention are coupled by guanidyl linkages, they will be resistant to cellular nucleases that specifically recognize phosphodiester linkages.

The ability of oligonucleosides to penetrate the cell membrane and their mechanism of penetration are critical considerations in developing these agents as therapeutic and diagnostic agents. While cell membranes are generally impermeable to charged molecules, this problem can be overcome for DNG or RNG oligonucleosides. These positively charged oligonucleosides can be annealed to a complementary oligonucleotide having a standard phosphate backbone prior to delivery into a host cell. The duplex then crosses the membrane. Once the oligonucleotide having a standard phosphate backbone is degraded by host cell nucleases, the DNG or RNG oligonucleoside can bind to its target sequence.

Further, the oligonucleosides of the present invention can be synthesized easily and in large quantities. Therefore, methods for large-scale synthesis of homomers or heteromers of the present invention can be commercially pursued.

In order that the invention described herein may be more fully understood, the following examples are set forth. It should be understood that these examples are for illustrative purposes only and are not to be construed as limiting the scope of this invention in any manner.

EXAMPLE 1

Materials and Methods

Synthesis

General procedures. All thin layer chromatography (TLC) was run with Merck silica gel 60 ($F_{254}$) plates. $^1$H NMR chemical shift assignments were referenced to dimethylsulfoxide (DMSO) (2.49 ppm). High resolution mass spectra were obtained from the U.C.L.A. mass spectrometry laboratory.

Figure 2A:
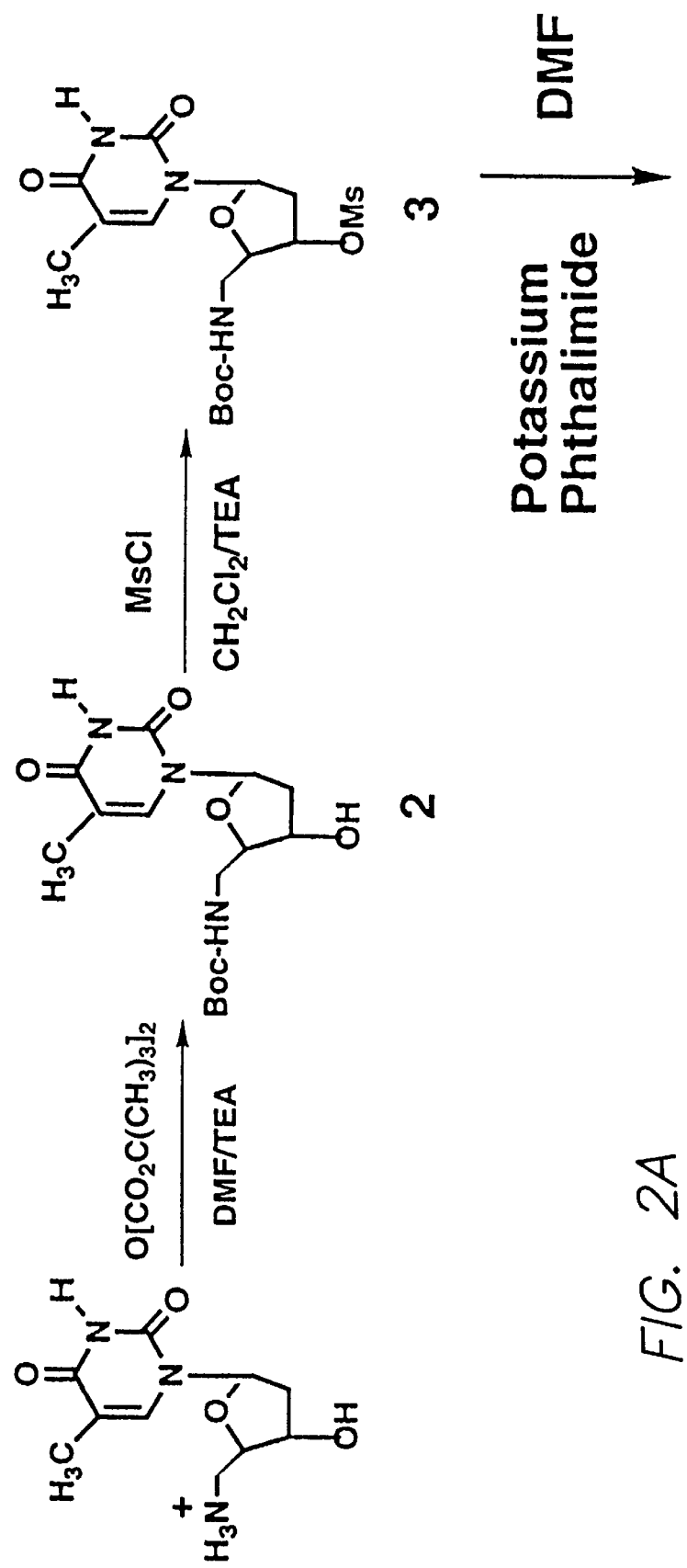
FIGS. 2A, 2B and 2C. General synthetic strategy for chain-extending intermediate thymidyl S-methylisothiourea derivative (9) of FIG. 1.

5'-t-Butyl carbamoyl-5'-deoxythymidine (2 of FIG. 2A). To a suspension of 5'-amino-5'-deoxythymidine (Horwitz, J. P.; Tomson, A. J.; Urbanski, J. A.; Chua, J.; (1962) *J. Org. Chem.* 27, 3045–3048) (4.0 g, 16.6 mmol) in 100 Ml of dry N,N-dimethylformamide (DMF) was added triethylamine (4.4 mL, 18.2 mmol) followed by dropwise addition of di-t-butyl dicarbonate (4.2 mL, 31.6 mmol).

The structure of 5'-t-Butyl carbamoyl-5'-deoxythymidine is as follows.

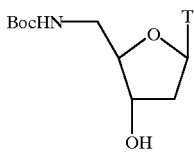

The resulting solution was stirred at room temperature for 30 minutes and then evaporated to dryness.

The residue was crystallized from water: 5.5 g (97%) yield; m.p.=164° C.; TLC (5% methanol in ethyl acetate), $R_f$=0.43; infrared (IR) (KBr) 3381, 1727, 1690, 1660, 1530, 1480, 1370, 1278, 1180, 1094 and 611 cm$^{-1}$; $^1$H NMR (DMSO-d$_6$) d 7.52 (1 H, s, 6-H), 7.05 (1 H, br t, carbamoyl N-H), 6.13 (1 H, t, J=6.9 Hz, 1'-H), 5.28 (1 H, d, J=4.0 Hz, 3'-OH), 4.13 and 3.73 (2 H, 2×m, 3'-H and 4'-H, no assignments made), 3.13 (2 H, m, 5'-Hs), 2.04 (2 H, m, 2'-Hs), 1.80 (3 H, s, methyl), 1.37 (9 H, s, t-butyl). high resolution mass spectroscopy (HRMS) (EI) m/e 341.1592 (M$^+$), calcd for $C_{15}H_{23}N_3O_6$ 341.1587.

5'-t-butyl carbamoyl-5'-deoxy-3'-O-mesyl-thymidine (3 of FIG. 2A) To a suspension of 2 (5.5 g, 16.11 mmol) in 100 mL of dry $CH_2Cl_2$ at 0° C. was added dry triethylamine (9.3 mL, 66.7 mmol) followed by careful dropwise addition of methanesulfonyl chloride (9.3 mL, 118 mmol). After warming to room temperature and stirring and stirring for 30 minutes, the completed reaction solution was washed with 100 mL of water.

The structure of 5'-t-butyl carbamoyl-5'-deoxy-3'-O-mesyl-thymidine is as follows (T represents thymidine).

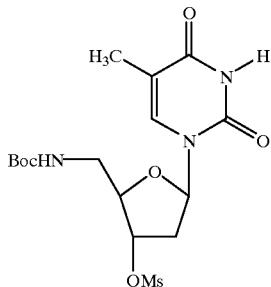

The $CH_2Cl_2$ layer was separated and the aqueous layer was extracted with $CH_2Cl_2$ (3×75 mL). The $CH_2Cl_2$ extracts were pooled, dried over $Na_2SO_4$ and evaporated. The residue was dissolved in 25 mL of ethyl acetate and filtered through a slurry of silica gel (3×7 cm) eluting with ethyl acetate.

The filtrate was evaporated and the residue was precipitated from $H_2Cl_2$-hexane: 5.83 g (86%) yield; m.p=141° C. (dec); TLC (ethyl acetate ), $R_f$=0.65; IR (Kbr) 3420, 3030, 1712, 1690, 1360, 1175, 1049, 960, 916 and 530 cm$^{-1}$; $^1$H NMR (DMSO-d$_6$) d. 7.56 (1 H, s, 6-H), 7.16 (1 H, br t, carbamoyl N-H), 6.13 (1 H, t, J=7.3 Hz, 1'-H), 5.22 (1 H, m, 3'-H), 4.06 (1 H, m, 4'-H), 3.31–3.18 (5 H, s and m, mesyl methyl and 5'-Hs), 2.43 (2 H, m, 2'-Hs), 1.80 (3 H, s, C(5)-methyl), 1.38 (9 H, s, t-butyl).

Figure 2B:
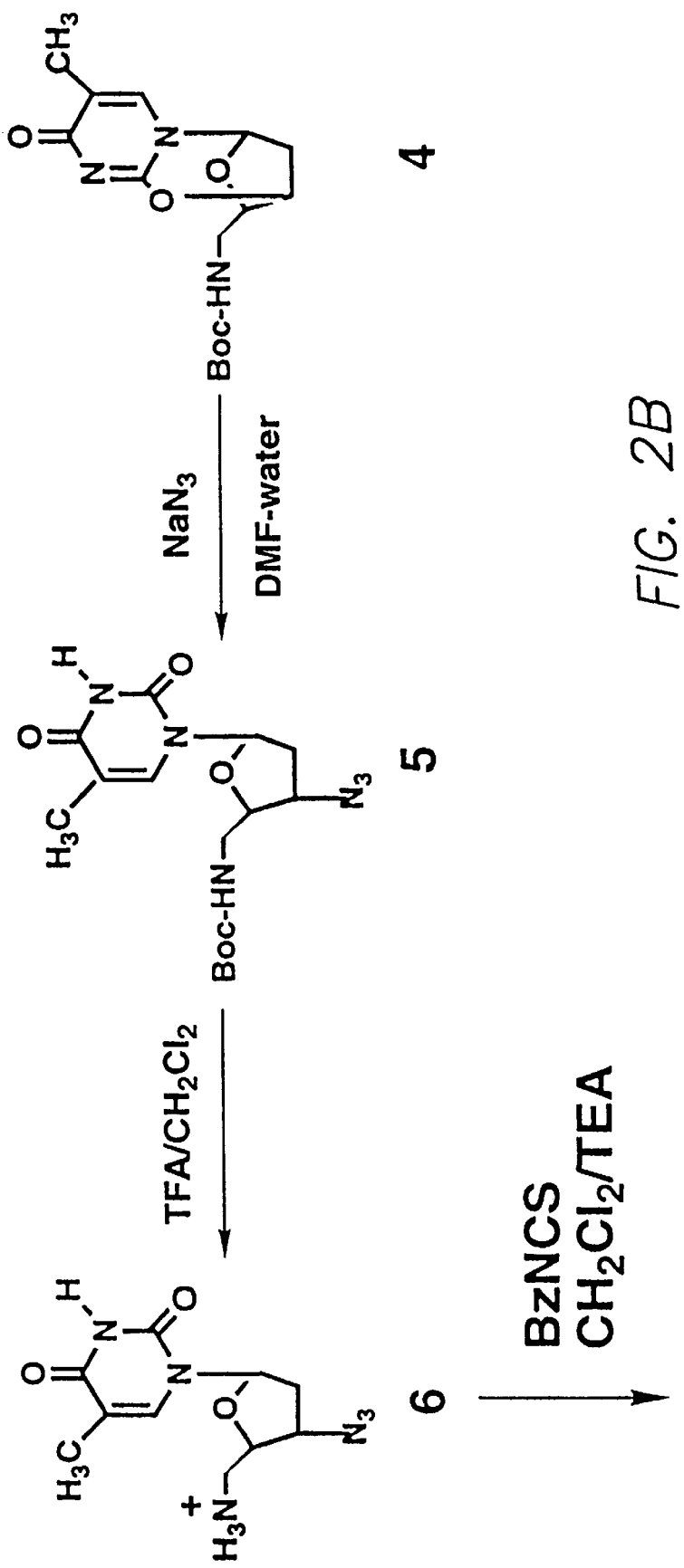

5'-t-Butyl carbamoyl-5'-deoxy-2,3'-anhydrothymidine (4 of FIG. 2B). To a solution of 3 (5.70 g, 13.6 mmol) in 60 M1 of DMF was added a solution of potassium phthalimide (10.3 g, 55.6 mmol) in 17.0 mL of water. The resulting solution was heated to 100° C. with stirring and then allowed to cool to room temperature and diluted with 300 mL of water.

The structure of 5'-t-Butyl-carbamoyl-5'-deoxy-2,3'-anhydrothymidine is as follows.

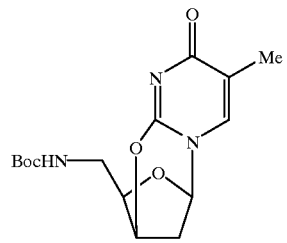

The phthalimide precipitate was filtered off and the filtrate was reduced to a ~100 mL and then extracted with ethyl acetate (8×150 mL). The pooled ethyl acetate extracts were dried over $Na_2SO_4$ and evaporated.

The residue was precipitated from ethyl acetate-hexane: 4.1 g (93%) yield; m.p.=82° C. (dec); TLC (n-butanol-water-acetic acid, (5:3:2)), $R_f$=0.54; IR (KBr) 3222, 1688, 1662, 1632, 1531, 1482, 1311, 1140, 880, 790 and 720 cm$^{-1}$; $^1$H NMR (DMSO-d$_6$) d 7.56 (1 H, s, 6-H), 7.07 (1 H, br t, carbamoyl N-H), 5.81 (1 H, d, J=2.9 Hz, 1'-H), 5.24 and 4.24 (2 H, 2×m, 2'-Hs), 3.12 (2 H, m, 5'-Hs), 1.75 (3 H, s, methyl), 1.36 (9 H, s, t-butyl). HRMS (EI) m/e 324.1575 (M+H)$^+$, calcd for $C_{15}H_{22}N_3O_5$ 324.1559.

3'-Azido-5'-t-butyl carbamoyl-3',5'-deoxy-thymidine (5 of FIG. 2B). To a solution of 4 (5.0 g, 15.5 mmol) in 50 mL of DMF was added a solution of NaN$_3$ (5.0 g, 76.9 mmol) in 10 mL of water. The resulting solution was stirred at 100° C. for 20 h, evaporated to dryness, and the residue was redissolved in 30 mL of water and extracted with ethyl acetate (4×70 mL). The pooled extracts were dried over Na$_2$SO$_4$ and evaporated.

The structure of 3'-Azido-5'-t-butyl carbamoyl-3',5'-deoxy-thymidine is as follows.

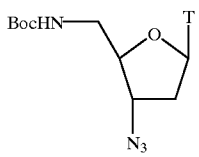

The residue was precipitated from ethyl acetate-hexane: 4.90 g (86%) yield; m.p.=66° C. (dec); TLC (10% hexane in ethyl acetate), R$_f$=0.56; IR (KBr) 3345, 2980, 2110, 1690, 1518, 1470, 1370, 1272, 1159 and 1090 cm$^{-1}$; $^1$H NMR (DMSO-d$_6$) d 7.52 (1 H, s, 6-H), 7.17 (1 H, br t, carbamoyl N-H), 6.05 (1 H, t, J=6.6 Hz, 1'-H), 4.29 and 3.75 (1 H 2×m, 3'-H and 4'-H, no assignments made), 3.23 (2 H, m, 5'-Hs), 2.32 (2 H, m, 2'-Hs), 1.81 (3 H, s, methyl), 1.38 (9 H, s, t-butyl). HRMS (CI) m/e 367.1733 (M+H)$^+$, calcd for C$_{15}$H$_{23}$N$_6$O$_5$ 367.1730.

5'-Amino-3'-azido-3',5'-deoxythymidine hydrochloride salt (6 of FIG. 2B). A solution of 5 (0.95 g, 2.60 mmol) dissolved in 30 mL of 30% trifluoroacetic acid in CH$_2$Cl$_2$ was stirred at room temperature for 20 minutes. The completed reaction was evaporated and the residue was dissolved in 30 mL of absolute ethanol. Concentrated HCl (0.30 mL) was added and the solution was evaporated to dryness to afford a brown solid: 752 mg (96%) yield; m.p=78° C. (dec); TLC (n-butanol-water-acetic acid, (5:3:2)), R$_f$=0.39; IR (KBr) 3400, 3000, 2090, 1675, 1462, 1263 and 1062 cm$^{-1}$; $^1$H NMR (DMSO-d$_6$) d 8.27 (3 H, br s, ammonium protons), 7.63 (1 H, s, 6-H), 6.13 (1 H, t, J=6.7 Hz, 1'-H), 4.57 and 3.96 (2 H, 2×m, 3'-H and 4'-H, no assignments made), 3.16 (2 H, m, 5'-Hs), 2.62–2.30 (2 H, 2×m, 2'-Hs), 1.80 (3 H, s, methyl). HRMS (CI) m/e 267.1205 (M+H)$^+$, calcd for C$_{10}$H$_{15}$N$_6$O$_3$ 267.1206.

The structure of 5'-Amino-3'-azido-3',5'-deoxythymidine hydrochloride salt is as follows.

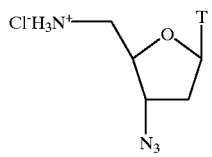

Figure 2C:
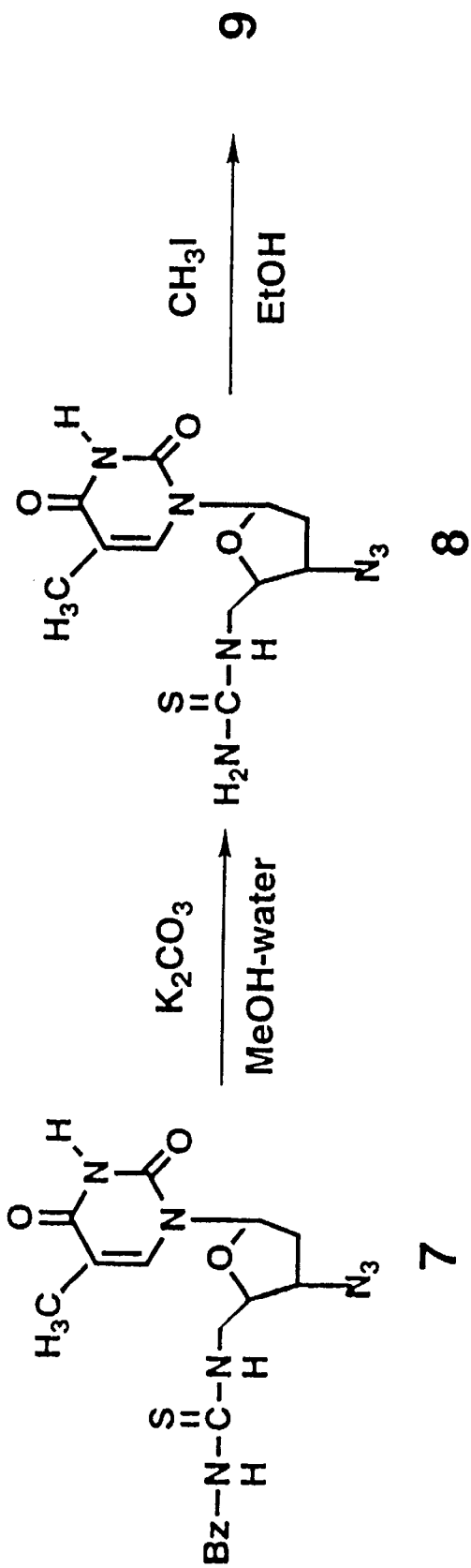

3'-Azido-5'-N-Benzoylthiourea-3',5'-deoxythymidine (7 of FIG. 2C). To a suspension of 6 (1.40 g, 4.62 mmol) in 60 mL of dry CH$_2$Cl$_2$ was added 0.65 mL of dry triethylamine followed by dropwise addition of benzoylisothiocyanate (0.67 mL, 5.00 mmol). The structure of 3'-Azido-5'-N-Benzoylthiourea-3',5'-deoxythymidine is as follows.

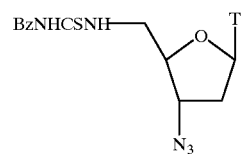

The suspension turned to a clear solution after a few minutes and the reaction was stirred at room temperature for a total of 30 minutes and washed with 40 mL of water. The aqueous layer was extracted with CH$_2$Cl$_2$ (2×100 mL).

The pooled extracts were dried over Na$_2$SO$_4$ and evaporated to dryness to afford a brown solid: 1.95 g (98w) yield; m.p=84° C. (dec); TLC (ethyl acetate), R$_f$=0.79; IR (KBr) 3180, 3045, 2106, 1695, 1550, 1518, 1272, 1176, 1072 and 712 cm$^{-1}$; $^1$H NMR (DMSO-d$_6$) d 7.93 and 7.56 (6 H, d and m, J=6.7 Hz for the doublet, phenyl and 6-H), 6.16 (1 H, t, J=6.7 Hz, 1'-H), 4.46 and 4.04 (4 H, 2×m, 3'-H, 4'-H and 5'-Hs, no assignments made), 2.41 (2 H, m, 2'-Hs), 1.73 (3 H, s, methyl). HRMS (CI) m/e 430.1295 (M+H)$^+$, calcd for C$_{18}$HN$_7$O$_4$S 430.1297.

3'-Azido-5'-thiourea-3',5'-deoxythymidine (8 of FIG. 2C). To a suspension of 7 (1.0 g, 2.33 mmol) in 40 mL of methanol was added a solution of 1.16 g of potassium carbonate in 16.0 mL of water. The mixture was stirred at room temperature for 30 minutes. The methanol was evaporated and the remaining aqueous solution was diluted to 50 mL with water and adjusted to pH 8 with acetic acid. The solution was extracted with ethyl acetate (3×100 mL). The pooled extracts were dried over Na$_2$SO$_4$ and evaporated.

The structure of 3'-Azido-5'-thiourea-3',5'-deoxythymidine is as follows.

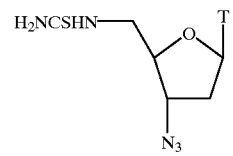

The residue was precipitated from ethyl acetate-hexane: 619 mg (82%) yield; m.p=113° C. (dec); TLC (n-butanol-water-acetic acid, (5:3:2)), R$_f$=0.78; IR (KBr) 3330, 3205, 2106, 1678, 1473, 1277 and 1085 cm$^{-1}$; $^1$H NMR (DMSO-d$_6$) d 8.91 (1 H, br s, 5'-NH), 7.41 (3 H, br s, 6-H and CONH$_2$), 6.13 (1 H, t, J=6.6 Hz, 1'-H), 4.47 and 3.91 (2 H, 2×m, 3'-H and 4'-H, no assignments made), 3.74 (2 H, m, 5'-Hs), 2.31 (2 H, m, 2'-Hs) , 1.78 (3 H, s, methyl). HRMS (CI) m/e 326.1034 (M+H)$^+$, calcd for C$_{11}$H$_{16}$N$_7$O$_3$S 326.1035.

3'-Azido-5'-S-methylisothiouronium-3',5'-deoxythymidine Iodide (9 of FIG. 2C). To a solution of 8 (280 mg, 0.86 mmol) in 12 mL of absolute ethanol was added methyl iodide (0.080 mL, 1.27 mmol). The reaction vial was sealed and the solution was allowed to stir for 14 h at room temperature.

The structure of 3'-Azido-5'-S-methylisothiouronium-3',5'-deoxythymidine iodide is as follows.

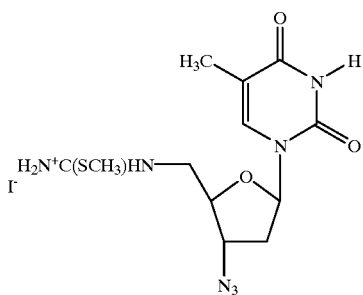

The completed reaction was evaporated to dryness and the residue was triturated with ether to afford a white solid: 326 mg (81%) yield; m.p.>80° C. (slow darkening); TLC (n-butanol-water-acetic acid, (5:3:2)), $R_f$=0.78; IR (KBr) 3160, 3050, 2118, 1698, 1650, 1475, 1280, 1094, 780 and 570 cm$^{-1}$; $^1$H NMR (DMSO-d$_6$) d 9.4–7.9 (br peak, N-H protons), 7.55 (1 H, s, 6-H), 6.14 (1 H, t, J=6.7 Hz, 1'-H), 4.42 and 3.93 (2 H, 2×m, 3'-H and 4'-H, no assignments made), 3.51 (2 H, m, 5'-Hs), 2.38 (2 H, m, 2'-Hs), 1.82 (3 H, s, methyl).

3'-Deoxythymidylyl-((3'-5')guanidyl)-3'-azido-3',5'-deoxythymidine Iodide (1 of FIG. 2A). The trifluoroacetate salt of 3'-amino-3'-deoxythymidine (76 mg, 0.213 mmol) and 9 (100 mg, 0.213 mmol) were dissolved in 0.50 mL of dry pyridine. Anhydrous triethylamine (300 μL) was added and the solution was stirred at 100° C. for 40 h. The reaction solution was cooled to room temperature and then diluted with 6.0 mL of isopropanol. The tan colored crystals of 1 were collected (48 mg). Hexane was added to the filtrate to produce another crop of crystals (57 mg).

The structure of 3'-Deoxythymidylyl-((3'-5')guanidyl)-3'-azido-3',5'-deoxythymidine Iodide is as follows.

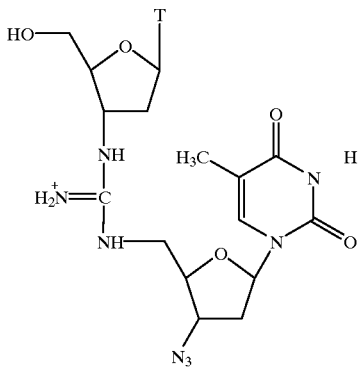

Total yield of 1: 105 mg (75%); m.p=115° C. (dec); TLC (isopropanol-water-ammonium hydroxide, (7:2:1)), $R_f$=0.43; IR (KBr) 3400, 3210, 3060, 2120, 1695, 1478, 1280, 1100, 785 and 570 cm$^{-1}$; $^1$H NMR (DMSO-d$_6$) d 11.37 and 11.32 (2 H, 2×s, thymidine ring N-Hs), 7.76, 7.56 and 7.45 (4 H, 3×br s, guanidinium protons), 7.67 and 7.46 (2 H, 2×s, 6-Hs), 6.15 and 6.10 (2 H, 2×t, J=6.0 and 6.5 Hz for the respective triplets, 1'-Hs), 5.40 (1 H, t, J=4.5 Hz, 5-OH), 4.32 and 4.20 (2 H, 2×m, 3'-Hs), 3.82 (2 H, m, 4'-Hs) 3.70–3.47 (4 H, 3×m, 2'-Hs), 1.80 and 1.78 (6 H, 2×s, methyl protons).

Addition of D$_2$O resulted in collapse of the thymidine ring N—H protons, the guanidyl protons and the 5'-OH. HRMS (FAB) m/e 533.2220 (M+H)$^+$, calcd for C$_{21}$H$_{29}$N$_{10}$O$_7$ 533.2221.

Molecular modeling.

Model building and computations were performed on a Silicon Graphics 4D/320GTX workstation using CHARMM (Brooks, B. R.; Bruccoleri, R. E.; Olafson, B. D.; States, D. J.; Swaminathan, S.; Karplus, M. (1983) *J. Comput. Chem.* 4, 187–217) v 22 (Adopted-Basis Newton Raphson (ABNR), steepest descents (SD) minimization, DNAH.RTF topology file) and QUANTA v. 3.3 (Nucleic Acid Builder, Molecular editor) programs (MSI, Waltham, Mass.).

Atom types C, NC and HC were used for the carbon, nitrogens and hydrogens of the guanidines, respectively. The X-ray structure for sodium thymidylyl- (5'>3')-thymidylate-(5') hydrate (pTpT), found in the Cambridge structural database (Medical Foundation of Buffalo, Buffalo N.Y.) as refcode THYTHY10 (Camerman, N.; Fawcett, J. K.; Camerman, A. (1976) *J. Mol. Biol.* 107, 601–621) was used to build a model for the dimeric DNG 1.

The phosphate PO$_4^-$ of the nucleotide linkage of pTpT was overlapped with a molecule of guanidine ((H$_2$N)$_3$C$^+$). Two nitrogens overlap with O3' and O5', while the carbon assumes a position near the phosphorus. The third —NH$_2$ lands in between the two charged oxygens of >PO$_4^-$.

The 5' terminal phosphate was truncated to an —OH, and an azide (—N$_3$) was placed onto the position of the O3' terminal atom. Coordinates for the azide moiety were taken from an X-ray structure of tri-O-acetyl-b-D-xylopyranosyl-azide (refcode ACXPAZ in the Cambridge structural database). (Luger, P.; Paulsen, H. (1976) *Acta Cryst. Sect. B* 32, 2774)

ABNR minimization was subsequently applied, with atom constraints on the —N$_3$ group to give the model of 1.

A Watson-Crick base-paired decameric duplex of B-DNA (d(Ap)$_{10}$·d(Tp)$_{10}$) was made in Nucleic Acid Builder. (Almarsson, Ö.; Bruice, T. C.; Kerr, J.; Zuckermann, R. N. (1993) *Proc. Natl. Acad. Sci. USA* 90, 7518–7522; Almarsson, Ö.; Bruice, T. C.(1993) *Proc. Natl. Acad. Sci. USA* 90, 9542–9546) Hybrids of DNA•DNG were built by the overlapping procedure described for 1, on the d(Tp)$_{10}$ strand of d(Ap)$_{10}$·d(Tp)$_{10}$ (for Watson-Crick duplex), or onto d(Tp)$_{10}$ strands in the structure of DNA d(Ap)$_{10}$·(d(Tp)$_{10}$)$_2$ triple helix (Raghunathan, G.; Miles, H. T.; Sasisekharan, V. (1993) *Biochemistry* 32, 455–462) (for Watson-Crick and Hoogsteen base paired triplexes).

The modified backbone was adjusted by SD minimization with atom constraints on the positions of nucleobases and ribose rings. Constraints were then removed (ribose rings first, then nucleobases) with added distance constraints for base pairs. ABNR algorithm was used in subsequent minimizations. A CHARMM .RTF for the DNG unit was written by comparison with DNAH.RTF.

Results

Figure 1B:
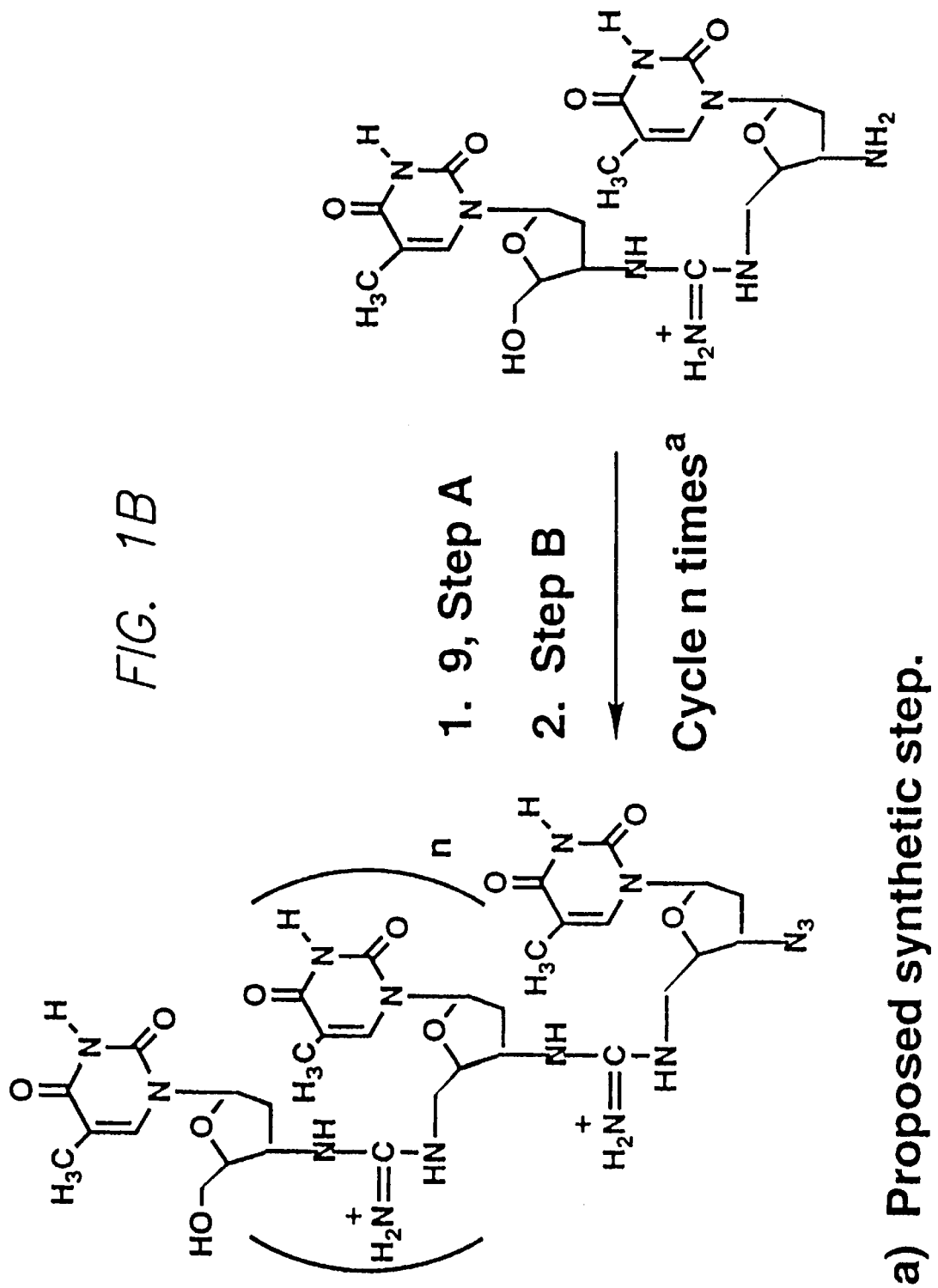

The general synthetic strategy for the formation of thymidyl DNG oligomers with a 5-OH terminal begins with the condensation reaction between 3'-amino-3'-deoxy-thymidine 10 and the thymidyl S-methylisothiourea derivative 9 (FIGS. 1A and 1B).

Chain extension is then possible by a two-step process, involving reduction of the 3'-azido group with Pd/C, in the presence of hydrogen, followed by condensation of the resulting amino dinucleoside with another equivalent of 9.

The chain-extending intermediate 9 was synthesized by an eight step pathway (FIGS. 2A, 2B and 2C) starting with 5'-amino-5'-deoxythymidine, which is conveniently prepared by the method of Horwitz et al. (J. Org. Chem 27: 3045–3048 (1962)).

Functionalization of the 3'-position as the azide first required protection of the 5'-amino group. Thus, treatment of 5'-amino-5'-deoxythymidine with di-tert-butyl dicarbonate in dry DMF afforded the Boc-protected amino derivative 2, which crystallized from water after evaporation of the DMF.

The reaction of 2 with methanesulfonyl chloride in $CH_2Cl_2$ produced the 3'-O-mesyl compound 3 which was then converted to the 2,3'-anhydronucleoside (Glinski, R. P.; Khan, M. S.; Kalamas, R. L.; (1973) *J. Org. Chem.* 38, 4299–4305) 4 upon treatment with potassium phthalimide in DMF. Ring opening of 4 with sodium azide in DMF-water (9) afforded the desired 3'-azido compound 5. The IR spectrum of 5 shows an absorbance at 2110 $cm^{-1}$, confirming the presence of the azido functionality. Compound 5 was converted to the S-methylisothiourea derivative by a four-step process beginning with the acid-catalyzed deprotection of 5 with trifluoroacetic acid in $CH_2Cl_2$.

The product from this reaction, the ammonium trifluoroacetate salt of 6, proved difficult to precipitate and was converted to the hydrochloride salt, which solidified upon evaporation from ethanol.

The N-benzoylthiourea derivative 7 was prepared by the treatment of 6 with benzoyl isothiocyanate in $CH_2Cl_2$ (Buschauer, A.; (1989) *J. Med. Chem.* 32, 1963–1970). Debenzoylation was achieved under alkaline conditions ($K_2CO_3$ in aqueous methanol (Buschauer et al., supra) to produce the thiourea 8.

The reaction of 8 with methyl iodide in absolute ethanol (Buschauer et al., supra) afforded the S-methylated derivative 9.

The trifluoroacetate salt of 3'-amino-3'-deoxythymidine 10 was prepared by a two step procedure starting with 3'-azido-3'-deoxy-5'-O-tritylthymidine. Reduction of the azido group with $H_2S$ in aqueous pyridine followed by removal of the 5'-trityl group with 30% trifluoroacetic acid in $CH_2Cl_2$ afforded 10 in good yield. However, this procedure offered no advantage over previous methods (Saneyoshi, M.; Fujii, T.; Kawaguchi, T.; Sawai, K.; Kimura, S.; in "*Nucleic Acid Chemistry*", part 4, New York, 1991; pp. 67–72) for the synthesis of 10.

Condensation of 9 with 10 in a solution of dry pyridine-triethylamine at 100° C. resulted in a 75% yield of dimeric thymidyl DNG 1.

The $^1H$ NMR spectrum of 1 identifies two thymidine moieties present in a 1:1 ratio. The four guanidinium N-H protons are present in the region of the spectrum between 7.76–7.45 ppm. An exchangeable triplet corresponding to the 5'-OH proton appears at 5.40 ppm.

The presence of the 3'-azido moiety was confirmed by an IR absorbance at 2120 $cm^{-1}$. High resolution mass spectral analysis of 1 provided the correct mass within 0.13 ppm. The HRMS analysis also provided an isotopic ratio of mass elements predicting the correct molecular formula: $C_{21}H_{29}N_{10}O_7$.

Models of 1 and the hybrid complexes of decameric DNG with DNA strands. A structure for 1 (0) was modeled using the X-ray crystal structures for the thymidylyl- (5'>3')-thymidylate-(5') dinucleotide (pTpT) and tri-O-acetyl-b-D-xylopyranosyl-azide (Camerman et al., supra; Luger et al., Acta Cryst. Sect. B 32: 2774 (1976).

Replacement of the phosphate of the nucleotide linkage with a guanidyl moiety mandates adjustment of the torsion angle C5'-N5'-C-N3' of the new linkage between the thymidine nucleosides. This angle is near –180° in the model of 1, and is required for planarity of the guanidine.

For comparison, the dihedral counterpart in pTpT, C5'-O5'-P-O3' or a, is between –39 and –73° in typical conformations of DNA and RNA (Saenger, W. "*Principles of Nucleic Acid Structure*" Springer Verlag, N.Y., 1984) and is –66.3° in the structure of pTpT. The change in the C5'-N5'-C-N3' torsion, brought about by energy minimization, causes the juxtaposition of the two thymine rings of 1 to alter, such that the bases are further apart than in the X-ray structure of pTpT.

Several options exist for the composition of base-paired oligomeric DNG-DNA hybrids. The following are combinations of decameric DNG and DNA strands which we consider at the present time (Scheme 1): (i) A hybrid duplex of thymidyl DNG $d(gT)_{10}$ with a $d(Ap)_{10}$ complement of DNA $(d(gT)_{10} \cdot d(Ap)_{10})$; (ii) A hybrid triplex of dsDNA with a $d(gT)_{10}$ as a Hoogsteen paired strand in the major groove of the DNA $(d(Tp)_{10} \cdot d(Ap)_{10} \cdot d(gT)_{10})$; and (iii) A hybrid triplex of $d(Ap)_{10}$ with two strands of $d(gT)_{10}(d(gT)_{10} \cdot d(Ap)_{10} \cdot d(gT)_{10})$.

Scheme 1

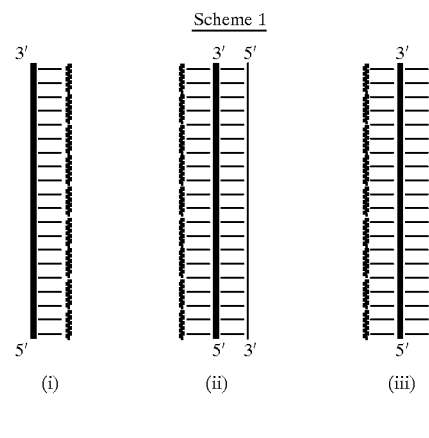

Key:

| : purine strand of DNA

| : pyrimidine strand of DNA

| : strand of DNG

— : Complementary base pair (Watson-Crick or Hoogsteen)

Figure 11:
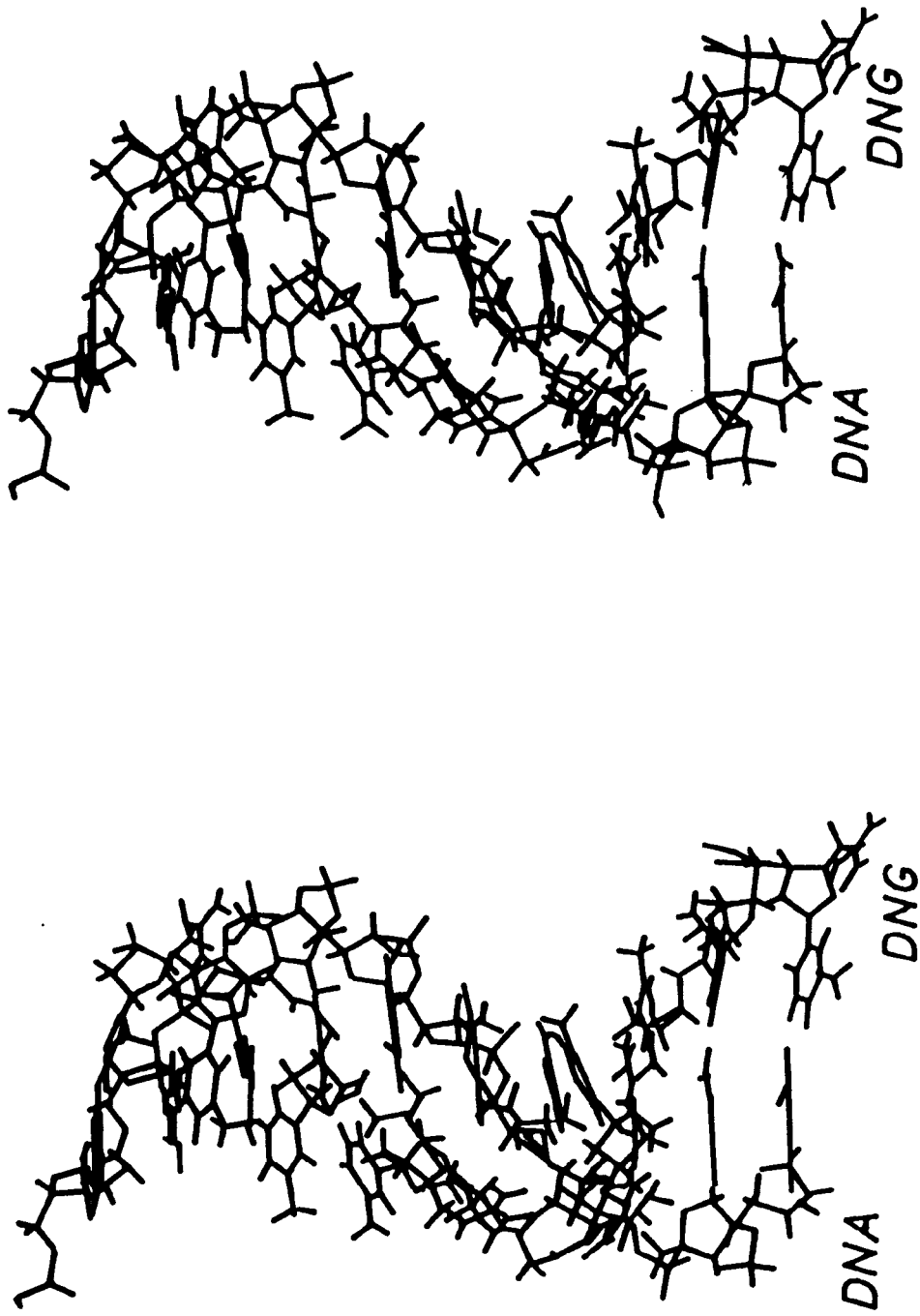
FIG. 11. Stereo view of the duplex hybrid of $(d(gT)_{10} \cdot d(Ap)_{10})$. The structure was computer generated from the structure of $B-(d(pT)_{10} \cdot d(Ap)_{10})$ by replacing the phosphate linkages by guanidyl linkages and energy minimization via ABNR in CHARMM.
Figure 12:
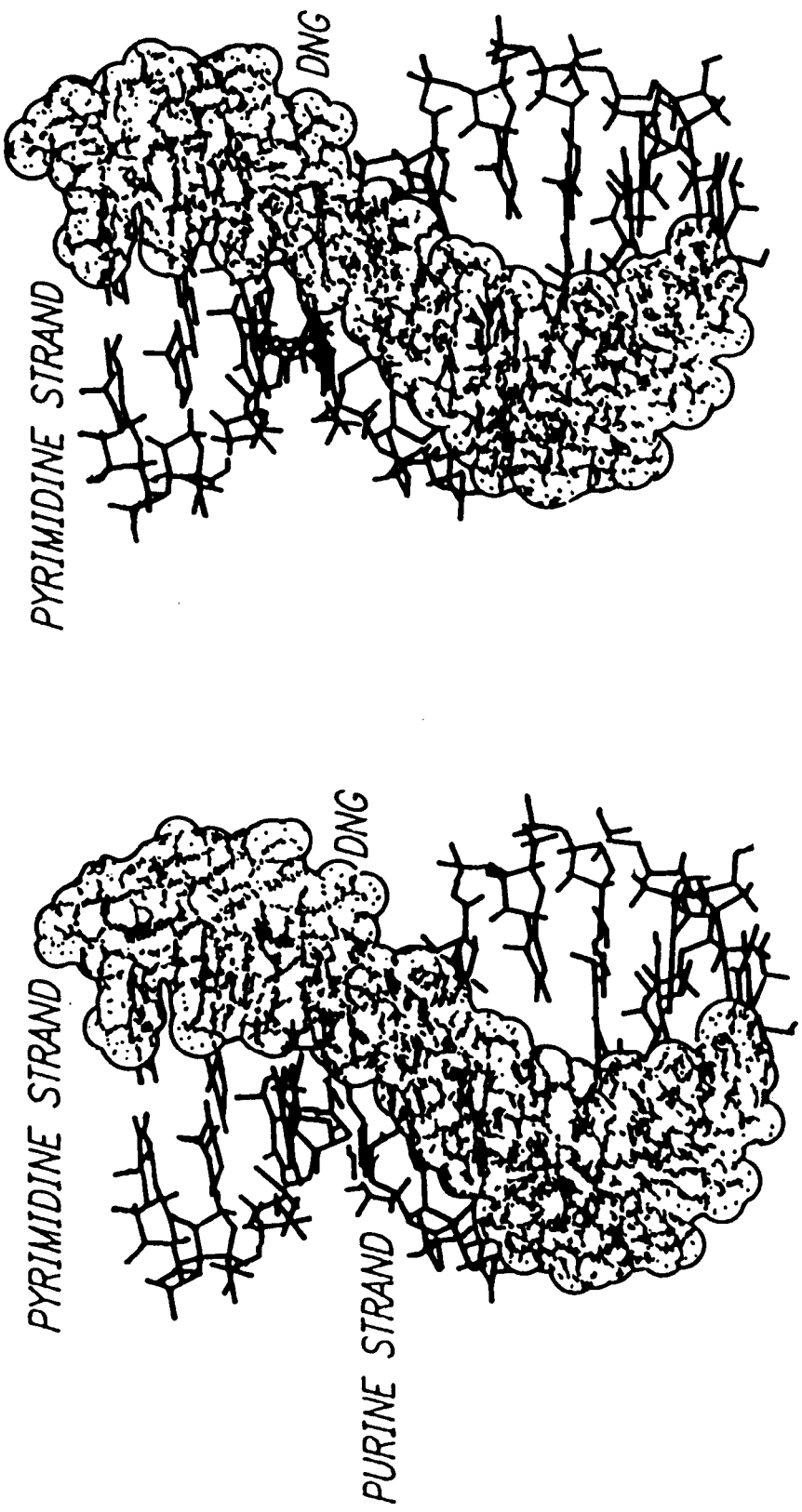
FIG. 12. Stereo view of the triple helical structure of $(d(Tp)_{10} \cdot d(Ap)_{10} \cdot d(gT)_{10})$. The model was created from the coordinates of $(d(Tp)_{10} \cdot d(Ap)_{10} \cdot d(Tp)_{10})$ after Ragunathan et al. Proc. Nat. Acad. Sci. USA 90: 9542–9546.

(i) FIG. 11 shows a model of $d(gT)_{10} \cdot d(Ap)_{10}$ after prolonged energy minimization (2000 steps) in CHARMM. The backbones of the two strands approach one another due to electrostatic interactions between repeating —O—($PO_2^-$)—O— and —NH—(C=$NH_2^+$)—NH— units. It is interesting to note that it is the minor groove that contracts.

In gas-phase calculations this contraction is from ~11.5 Å to ~4 Å with retention of Watson-Crick base-pairing. These electrostatic interactions should be attenuated to some extent in water. The sugar puckering of the DNA portion remains the characteristic C2'-endo (as in B-DNA), whereas the ribose rings of the DNG strands resemble an O4'-endo conformation, with the five-membered rings approaching flat geometries. In the gas phase calculations a repeating hydrogen bond between N(5')H to O(4') in the same residue is observed. The latter may be responsible for the conversion of ribose sugar puckering from C(2')-endo toward O(4')-endo.

(ii) Building of $d(Tp)_{10} \cdot d(Ap)_{10} \cdot d(gT)_{10}$ ensued from the structure proposed for the $d(Tp)_{10} \cdot d(Ap)_{10} \cdot d(Tp)_{10}$ triple helix of DNA (Raghunathan et al., supra). The guanidinium ions of the Hoogsteen base-paired $d(gT)_{10}$ strand in the major groove of the decameric dsDNA reside quite near the phosphates of the purine strand, such that $d(Ap)_{10}$ and $d(gT)_{10}$ experience electrostatic attractions between the backbones of one another.

Energy minimization resulted in the model of 2. The structure reveals enforced $d(Ap)_{10}$ and $d(gT)_{10}$ backbone interactions. The Watson-Crick paired $d(Tp)_{10}$ is remote from the guanidine backbone of $d(gT)_{10}$ and is not involved in electrostatic interactions in the complex to any significant extent.

(iii) We finally consider the possible hybridization of $d(gT)_{10}$ with a purine strand of ssDNA, as well as strand invasion into dsDNA by $d(gT)_{10}$. A precedent from the recent antisense/antigene literature for antagonistic behavior toward dsDNA is found in the case of peptide-nucleic acids (PNA), Almarsson et al., Proc. Natl. Acad. Sci. USA 90, 9542 (1993), Almarsson and Bruice, Proc. Natl. Acad. Sci. USA 90, 9542 (1993).

In the final complex, a central triple helix is produced, leaving an extruded strand of ssDNA. Additional electrostatic interactions would be gained, due to the presence of two anionic DNA strands and two cationic DNG strands in the same complex.

The presented models for decameric duplexes and triplexes serve to indicate the possible modes of interaction of DNG polymers with DNA.

Attenuation of the strong electrostatic effect should be resolved by interspersing nucleotide sequences into a DNG oligomer. The lengthening of the base separations in A-RNA vs. B-DNA (Saenger, suDra) suggest that DNG should exhibit specificity for DNA over RNA.

The absence of the 2'-OH in DNG structures also makes A-conformations of the ribose rings less likely to occur in the polymer.

EXAMPLE 2

This example is a prophetic example which teaches detection of HTLV-I anti-sense RNA in a HTLV-I infected cell using the polynucleoside chain of the invention Transcripts from HTLV-1 proviral genomes can be detected from the "anti-sense" strand as well as the "sense" strand that encodes the gag-pol-env genes. Labeled DNG oligonucleoside probes may be used to determine whether HTLV-I anti-sense RNA accumulates in infected cells using poly(A)+RNA blots of SLB1 (an HTLV-I positive human T cell line) and Molt4 (an HTLV-I negative human T cell line) RNA.

RNA can be isolated from the T cell lines and poly(A)+ RNA selected using standard procedures (Sambrook, Fritsch, and Maniatis, Eds. Molecular Cloning, Cold Spring Harbor Press, 1989). One microgram of poly(A)+enriched RNA from each cell line may be loaded in a 1.2% agarose/2.2M formaldehyde gel and processed for blot analysis. The blot may be cut into strips having one lane of each RNA, Molt4 and SLB1. The blots will be hybridized at a temperature, ionic strength, probe concentration, and for a characteristic time. The precise parameters will be empirically determined as they are based on a the length and base composition, in particular the percentage of the molecule comprised of G's and C's, of the probe molecule (Maniatis, Sambrook, Fritsch, and Maniatis, Molecular Cloning: A Laboratory Manual, p. 11.45–49, Cold Spring Harbor Press (1989)). However, these parameters can be easily and routinely determined by one skilled in the art. As an example of conditions that can be used, an oligonucleotide 24 nucleotides in length could be hybridized for 6–8 hours at 42° C. in 6× SSC (1× SSC: 0.15M NaCl, 0.015M NaCitrate), 0.1% sodium dodecyl sulfate (SDS), and 0.5% (w/v) non-fat dry milk.

The oligonucleodides containing DNG can be labeled with gamma-$^{32}$P-ATP by kinasing the oligonucleoside molecules at their 5' ends. Alternatively, the oligonucleosides can be radiolabeled by using terminal deoxynucleotidyl transferase to attach a labeled alpha-$^{32}$PDNTP to the 3'OH end of the oligonucleoside.

Oligonucleosides containing RNGs and DNGs could also be labeled by using non-radioactive methods. For example, 11-digoxigenin-11-DUTP, a nucleotide analog, can be added to the 3' end of DNG's using terminal deoxynucleotidyl transferase using a procedure developed by Bohringer-Mannheim (Indianapolis, Ind.). The digoxigenin-labeled probe can then be detected using an antibody specific for digoxigenin moiety. The antibody is conjugated to a reporter molecule, such as alkaline phosphatase that is detected upon incubation with an appropriate substrate.

Following hybridization, strips can be washed to remove non-specifically bound probe molecules using empirically determined conditions. For example, the blots may be washed three times each for five minutes at 42° C. in 2× SSC, 0.1% SDS.

The strips will then be processed for detection of the probe molecule. In the case of radiolabeled probes, the strips will be exposed to XRay film.

As one skilled in the art will appreciate, DNG and RNG probes utilizing these methods can be also be used to recover cDNA and genomic clones containing these sequences.

EXAMPLE 3

Prophetic example of hybridization analysis to PSβG RNA from placental tissue using polynucleoside chains of the invention PSβG is a glycoprotein expressed during pregnancy and at particularly high levels in certain gestational trophoblastic diseases, such as hydatiform moles. A sensitive assay to detect PSβg RNA levels in placental tissue is a useful tool for diagnosing such diseases.

RNG or DNG oligounucleosides of the invention that are specific for the PSβG transcript can be used to detect PSβG RNA in placental tissue. Total RNA from two placental samples, one from a healthy term pregnancy and the other carrying a hydatiform mole will be isolated and poly(A)+ RNA selected using standard protocols (Sambrook, Fritsch, and Maniatis). One microgram of poly(A)+enriched RNA from the sample of infected cells may be loaded in a 1.4% agarose/2 2M formaldehyde gel and processed for blot analysis. The blot may be cut into strips having one lane of each source of RNA.

The blots may then be hybridized at a temperature, ionic strength, probe concentration, and for a specified time. The precise parameters will be empirically determined as they are based on a the size and base composition of the probe molecule (Maniatis, Sambrook, supra). However, these parameters can be easily and routinely determined by one skilled in the art. As an example of conditions that can be used, an oligonucleotide 24 nucleotides in length could be hybridized for 6–8 hours at 42° C. in 6× SSC (1× SSC: 0.15M NaCl, 0.015M NaCitrate), 0.1% sodium dodecyl sulfate (SDS), and 0.5% (w/v) non-fat dry milk.

The probe is a polynucleoside version of the invention containing a portion of the published PSβG sequence of U.S. Pat. No. 5,141,849. It is synthesized following the protocol described herein.

The probe can be labeled using gamma$^{32}$P-ATP by kinasing molecules at their 5' ends. Alternatively, oligonucleosides containing DNG can be radiolabeled by using terminal deoxynucleotidyl transferase to attach alpha-$^{32}$PdNTPs to the 3'OH ends of the molecule.

Oligonucleosides containing RNGs or DNGs could also be labeled by using non-radioactive methods. For example, 11-digoxigenin-11-DUTP, a nucleotide analog, can be added to the 3' end of oligonucleosides containing DNGs using terminal deoxynucleotidyl transferase using a procedure developed by Bohringer-Mannheim (Indianapolis, Ind.). The digoxigenin-labeled probe can then be detected using an antibody specific for digoxigenin moiety. The antibody is conjugated to a reporter molecule, such as alkaline phosphatase that is detected upon incubation with an appropriate substrate.

Following hybridization, strips can be washed to remove non-specifically bound probe molecules using empirically determined conditions. For example, the blots may be washed three times each for five minutes at 42° C. in 2× SSC, 0.1% SDS.

The strips will then be processed for detection of the probe molecule. In the case of radiolabeled probes, the strips will be exposed to XRay film.

EXAMPLE 4

Materials and Methods

General procedures. All TLC was run with Merck silica gel ($F_{254}$) plates. $^1$H NMR were obtained on Varian Gemini-200 or General Electric GN-500 spectrophotometers in DMSO-$d_6$ at 25° C. unless otherwise specified. Chemical shifts (ppm) were referenced to DMSO (2.49 ppm). Purified DNA oligonucleotides were purchased from UCSF Biomolecular Resource Center and from Pharmacia. The concentrations of DNA and DNG oligonucleotide stock solutions were determined at 67° C. with a Cary-14 UV/vis spectrophotometer from the Beer-Lambert law using known extinction coeffients for individual nucleotides at 260 nm (Beaven, G. H., Holiday, E. R., and Johnson, E. A., (1955) in *The Nucleic Acids: Chemistry & Biology*, I, eds. Chargaff, E. & Davidson, J. N. (Academic Press, New York), pp. 493–553.). Mass spectra were obtained from the mass spectrometry laboratory of the University of California at Los Angeles.

Nomenclature. The guanidyl linkage of DNG oligonucleotides is specified by the letter "g" while thiourea-linked oligonucleotides are specified by the letter "t".

Synthesis. 3'-Azido-5'-isothiocyano-3',5'-deoxythymidine (2; Scheme 2), To a suspension of 5'-amino-3'-azido-3',5'-deoxythymidine (2) (2.0 g, 6.60 mmol) in 200 ml of dry methylene chloride, 2.0 ml of dry triethylamine was added followed by carbon disulfide (20 ml) and 1,3-dicyclohexylcarbodiimide (1.48 g, 7.17 mmol). The resulting solution was stirred at room temperature for 30 min and then evaporated to dryness in vacuo. The residue was dissolved in a minimum volume of ethyl acetate and chromatographed through a silica gel column eluting with ethyl acetate. The product fractions were evaporated to afford a homogenous oil: yield, 1.62 g (79%) ; TLC (ethyl acetate) $R_f$=0.66; IR (NaCl plate) 3192, 3047, 2930, 2106, 1699, 1470, 1271, 1084 cm$^{-1}$; $^1$H NMR d 7.45 (1 H, s, 6-H), 6.17 (1 H, t, J=6.7 Hz, 1'-H), 4.48 (1 H, m, 3'-H) , 4.02 (3 H, m, 4'-H and 5'-Hs), 2.43 (2 H, m, 2'-Hs), 1.82 (3 H, s, methyl protons); HRMS (CI) m/e 309.0759 (M+H)$^+$, calcd. for $C_{11}H_{13}N_6O_3S$ 309.0769.

Trityl-d ($T_tT$) -azido (3). A solution of 2 (1.18 g, 3.85 mmol) and 5'-O- trityl-3'-amino-3'-deoxythymidine (4) (1.86 g, 3.85 mmol) in 15 ml of dry N,N-dimethylformamide (DMF) was stirred for 3.0 hr at 80° C. The solution was evaporated to dryness and the residue was precipitated from ethyl acetate-ether: yield, 2.60 g (85%); m.p. 148° C. (dec); TLC (10w methanol in ethyl acetate) $R_f$=0.48; IR (KBr) 3344, 3059, 2105, 1697, 1471, 1270, 1079, 705 cm$^{-1}$; $^1$H NMR d 7.65–7.10 (17 H, m, 6-Hs and trityl protons), 6.22 and 6.11 (2 H, 2×t, J=6.74 and 6.74 Hz, 1'-Hs), 4.44–3.09 (8 H, 3'-, 4'- and 5'-Hs), 2.48–2.12 (4 H, 2×m, 2'-Hs), 1.81 and 1.40 (6 H, 2×s, methyl protons); HRMS {fast-atom bombardment (FAB)} m/e 792.2934 (M+H)$^+$, calcd for $C_{40}H_{42}N_9O_7S$ 792.2928.

Trityl-d($T_tT$)-amino (4). A thin stream of hydrogen sulfide gas was bubbled into a solution of 3 (2.50 g, 3.16 mmol) in 50% aqueous pyridine (80 ml) at room temperature for 3.0 hr. The solution was filtered and the filtrate was evaporated to dryness. The residue was precipitated from ethyl acetate-ether: yield, 2.21 g (91%); m.p. 152° C. (dec); TLC (n-butanol/water/acetic acid, 5:3:2) $R_f$=0.48; IR (KBr) 3060, 3035, 2927, 1699, 1544, 1473, 1448, 1269, 1076, 769, 706 cm$^{-1}$; $^1$H NMR d 7.55–7.26 (17 H, m, 6-Hs and trityl protons), 6.18 (2 H, m, 1'-Hs), 4.00–3.13 (8 Hs, 3'-, 4'- and 5'-Hs), 2.24–1.96 (4 H, m, 2'-Hs), 1.80 and 1.40 (6 H, 2×s, methyl protons); HRMS (FAB) m/e 766.3057 (M+H)$^+$, calcd for $C_{40}H_{44}N_7O_7S$ 766.3023.

Trityl-d($T_t$)$_2$T-azido (5). A solution of 4 (1.16 g, 1.52 mmol) and 2 (0.515 g, 1.67 mmol) was stirred in dry DMF for 4.0 hr at 80° C. The solution was evaporated to dryness and the residue was precipitated from ethyl acetate-ether: yield, 1.31 g (80%); m.p. 180° C. (dec); TLC (n-butanol/ water/acetic acid, 5:3:2) $R_f$=0.77; IR (KBr) 3060, 2106, 1697, 1545, 1475, 1449, 1365, 1270, 1083 cm$^{-1}$; $^1$H NMR d 8.00–7.22 (18 H, 6-Hs and trityl protons) 6.18 and 6.083 (3 H, m and t, J=6.5 Hz for the t, 1'-Hs) 5.08–3.37 (12 H, 3'-, 4'- and 5'-Hs), 2.46, 2.31 and 2.18 (6 H, 3×m, 2'-Hs), 1.81, 1.80 and 1.45 (9 H, 3×s, methyl protons); HRMS (FAB) m/e 1074.3636 (M+H)$^+$, calcd for $C_{51}H_{56}N_{13}O_{10}S_2$ 1074.3714.

Trityl-d($T_t$)$_4$T-azido (9). Hydrogen sulfide gas was bubbled into a solution of 5 (1.31 g, 1.22 mmol) in 40 ml of 50% aqueous pyridine for 4.0 hr. The reaction solution was filtered and the filtrate was evaporated affording the amine (6) {TLC (n-butanol/water/acetic acid, 5:3:2) $R_f$=0.57}, which was dissolved in 15 ml of dry DMF containing 2 (451 mg, 1.46 mmol). A few drops of triethylamine was added to neutralize trace amounts of acid. The solution was stirred at 65° C. for 4.0 hr after which time the solvent was evaporated. The residue was triturated with 50 ml of hot methanol. After cooling the mixture to room temperature, 50 ml of ether was added. The precipitate (7) was collected: yield, 1.38 g (84%) for the two-step process: TLC (n-butanol/water/acetic acid, 5:3:2) $R_f$=0.74.

The solid tetramer 7 from above was dissolved in 30 ml of 50% aqueous pyridine and the azido moiety was reduced as described above for compound 5. The resulting amine 8 was dissolved in 20 ml of dry DMF containing 2 (451 mg, 1.46 mmol) and stirred at 65° C. for 4.0 hr. After evaporating the DMF, the residue was precipitated from DMF-methanol: yield, 1.41 g (84%) for the two-step reduction/coupling process; m.p.>200° C. (slow dec); TLC (n-butanol/ water/ acetic acid, 5:3:2) Rf=0.74; IR (KBr) 3061, 2107, 1704, 1552, 1472, 1270, 1090, 769, 706 cm$^{-1}$; $^1$H NMR (50° C.) d 7.98–7.22 (20 H, 6-Hs and trityl protons), 6.22–6.07 (5 H, m and t, J=6.5 Hz for the t, 1'-Hs) , 5.07–3.18 (20 H, 10×m, 3'-, 4'- and 5'-Hs), 2.40–2.10 (10 H, 4×m, 2'-Hs), 1.81, 1.79 and 1.43 (15 H, 3×s, methyl protons); HRMS (FAB) m/e 1638.5233 (M+H)$^+$, calcd for $C_{73}H_{84}N_{21}O_{16}S_4$ 1638.5287.

d($T_t$)$_4$T-azido (10). A solution of 9 (220 mg, 0.134 mmol) in 8.0 ml of 30% trifluoroacetic acid in methylene chloride was stirred at room temperature for 15 min. Methanol (12 ml) was added and the crystals that formed were collected and rinsed with isopropanol: yield, 163 mg (87%); m.p.>200° C. (slow dec); TLC (n-butanol/water/acetic acid, 5:3:2) $R_f$=0.70; IR (KBr) 3331, 3065, 2107, 1704, 1553, 1473, 1366, 1271, 1088, 772 cm$^{-1}$; $^1$H NMR d 7.77, 7.52, 7.48 and 7.46 (5 H, 4×s, 6-Hs), 6.23–6.06 (5 H, m, 1'-H), 5.10–3.44 (21 H, 5'-OH, 3'-, 4'- and 5'-Hs), 2.4–2.1 (10 H, m, 2'-Hs), 1.80 and 1.77 (15 H, 2×s, methyl protons); MS (FAB) m/e 1396.4173 (M+H)$^+$, calcd for $C_{54}H_{70}N_{21}O_{16}S_4$ 1396.4192.

d(T$_g$)$_4$T-azido (1). Compound 10 (40 mg, 0.0287 mmol) was added to 0.5 ml of peracetic acid solution (32 wt. % in dilute acetic acid, Aldrich) previously cooled to 0° C. The resulting solution was stirred for 15 min at 0° C. Methanol (4.0 ml) was added and the crystals of 11 that formed were collected and rinsed with methanol: yield, 43 mg (94%). Thirty milligrams of 11 (0.0189 mmol) was dissolved in 1.0 ml of concentrated ammonium hydroxide and stirred in a sealed tube at 65° C. for 14 hr. The white crystals that formed were collected and rinsed with water: yield, 24 mg (77%). Conversion of 1 into its water-soluble hydrochoride salt form was accomplished by suspending 1 in water and adding dilute HCL solution until the sample dissolved. An analytical sample was prepared by preparative HPLC using an Alltech WCX cation exchange column employing 0.80 M ammonium acetate buffer, pH 5.0, as the mobile phase. The major component was isolated and ammonium acetate was removed from the DNG sample by repetitive evaporations from water; m.p.>150° C. (slow dec); IR (KBr) 3356, 3211, 2966, 2826, 2108, 1674, 1502, 1467, 1355, 1090, 789 cm$^{-1}$; $^1$H NMR (D$_2$O) d 7.79, 7.62 and 7.60 (5 H, 3×s, 6-Hs), 6.32 and 6.25 (5 H, t and m, J=5.5 Hz for the t, 1'-Hs), 4.78–3.70 (20 H, 3'-, 4'- and 5'-Hs), 2.93–2.50 (10 H, 3×m, 2'-Hs), 2.06 (15 H, s, methyl protons). The guanidyl carbons are observed beween 156.46 and 156.41 ppm in the $^{13}$C NMR spectrum (D$_2$O); MS (FAB) m/e 1328.60 (M+H)$^+$, calcd for $C_{54}H_{74}N_{25}O_{16}$ 1328.56.

Electrophoresis. The electrophoretic mobilities of the DNG oligonucleotides d(Tg)$_4$T-azido (1) and d(TgT)-azido (2) and the DNA oligonucleotides d(TpT) and d(Tp)$_4$T (2.9×10$^{-6}$ M in bases, each) were compared on a 4.5% D600 (a proprietary acrylamide polymer solution of AT Biochem) horizontal gel (0.088 M NH$_4$OAc, pH 5.8). The oligonucleotides were electrophoresed through this medium in its polymerized form for 2 hr at a constant 1.5 V/cm. The separated oligonucleotides were observed by "UV-shadowing" on an ultraviolet transilluminator emitting at 254 nm.

Thermal Denaturation Studies. Plots of A$_{260}$ vs T (°C.) for 1 in the presence of poly(dA), p(dG)$_{12-18}$ poly(dI), poly(dC), or poly(dT) were obtained at pH 7.0 (0.01 M K$_2$HPO$_4$) using a Perkin-Elmer UV/vis spectrophotometer in conjuction with a NIST digital thermometer (accurate to ±0.2° C.). The concentration of each of the oligonucleotides was 4.17×10$^{-5}$ M in bases. The ionic strength ($\mu$) of samples was adjusted using an appropriate concentration of KCl. In a typical experiment, a solution of 1 and a DNA oligomer was heated to 93° C. and allowed to cool to 5° C. over several hours. Data points were then collected as the temperature was raised at the rate of ca. 1° C./5 min. The data points which comprise each curve were then computer fit to eq 1 (1 hyperchromic transition) or eq 2 (2 hyperchromic transitions) which optimizes for the inflection points for a $$A_{260} = \frac{a_1}{1 + e^{b_1(T-T_{m1})}} + d \qquad (1)$$

$$A_{260} = \frac{a_1}{1 + e^{b_1(T-T_{m1})}} + \frac{a_2}{1 + e^{b_2(T-T_{m2})}} + d \qquad (2)$$

curve (T$_{m1}$ and T$_{m2}$ in the case of DNG), the change in absorbances between inflection points (a$_1$ and a$_2$), the slope coefficients (b$_1$ and b$_2$), and the absorbance at high temperature (d).

Synthesis. The synthesis of the thymidyl DNG dimer via a condensation reaction between 3'-amino-3'-deoxythymidine and 3'-azido-5'-S-methylisothiouronium-3', 5'-deoxy-thymidine was described (Dempcy, R. O., Almarsson & Bruice, T. C. (1994) *Proc. Natl. Acad. Sci. USA* 91, 7864–7868.) Chain extension from the dimer was proposed to follow a cyclic two-step process involving reduction of the 3'-azido moiety to the amine, followed by another condensation reaction. This synthetic strategy succeeded in affording the DNG trimer {d(T$_g$)$_2$T-azido} (Crooke, S. T. (1993) *FASEB J.* 7, 533–539; Glinski, R. P.; Khan, M. S.; Kalamas, R. L.; Sporn, M. B. (1973) *J. Org. Chem.* 38, 4299–4305. The 3'-azido analogue in this reference was reduced with Pd/C, H$_2$ (g) in ethanol). The polar and organic-solvent insoluble nature of the growing cationic chain rendered purification of desired oligomers difficult. To overcome this problem, a new synthetic route was developed in which a pentameric thymidine oligomer was constructed with a neutral 5'-3' thiourea backbone (Scheme 2) via a cyclic process. Thus, the reaction between 3'-amino-5'-O-trityl-3'-deoxythymidine (4) and the 5'-isothiocyano derivative (2) afforded the thiourea-linked dimer (3). Reduction of the 3'-azido moiety with hydrogen sulfide in aqueous pyridine yielded the dimer amine (4). Condensation of 4 with a slight excess of 2 produced the chain-extended oligomer (5). Two additional rounds of the reduction/condensation cycle afforded the desired pentameric oligomer (9). The thiourea backbone was then converted to a guanidyl backbone by a two-step process involving oxidation of the thiourea linkages with peracetic acid {forming the aminoiminosulfonic acid derivative (11)} followed by amidation, forming the DNG oligomer (1).

Figure 13:
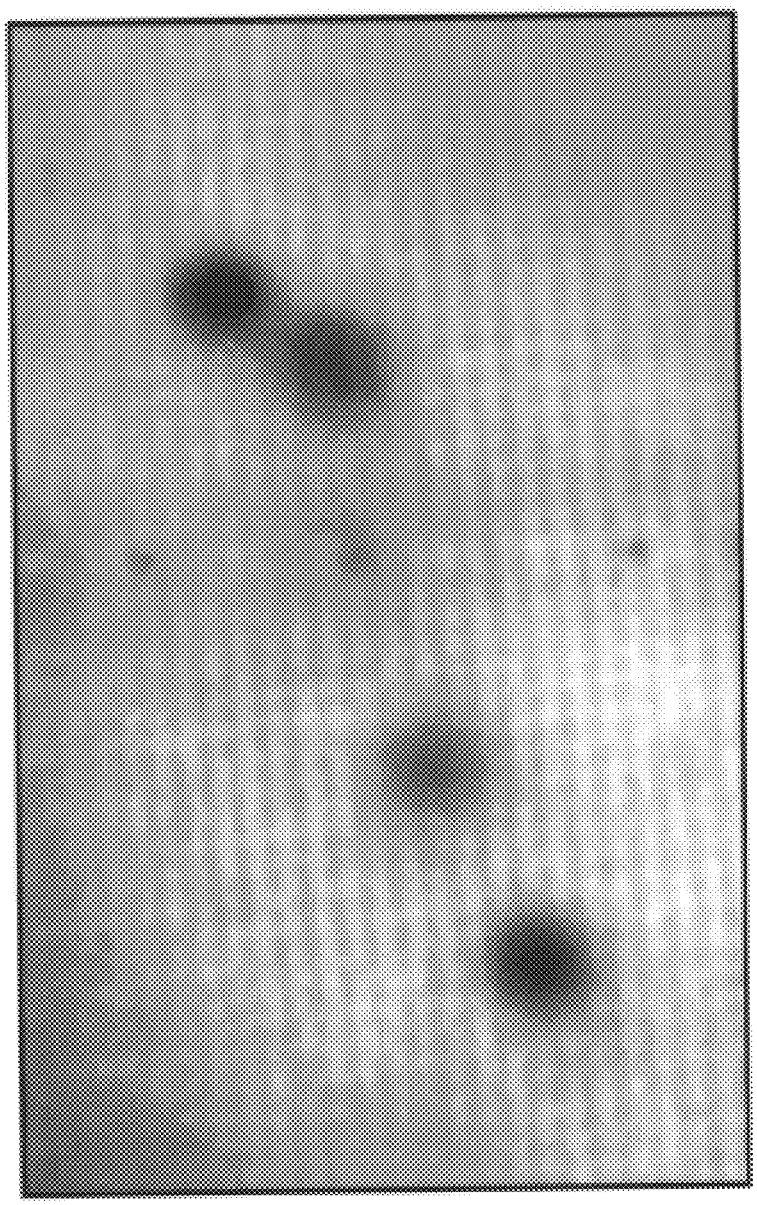
FIG. 13. The electrophoretic mobilities of the DNG oligonucleotides $d(Tg)_4$T-azido (1) and d(TgT)-azido (lanes 1 and 2) and the DNA oligonucleotides d(TpT) and d(Tp)$_4$T (lanes 3 and 4). Between 1 and 2×10$^{-7}$ moles (in bases) of each oligonucleotide were loaded into adjacent wells in the center (Origin) of the gel.

Electrophoresis. The electrophoretic behavior of DNG migrating through a polyacrylamide gel was compared to the migration of DNA (FIG. 13). The respective oligomers migrate in opposite directions. Both dimeric and pentameric DNG molecules migrate towards the cathode while the analogous DNA oligonucleotides travel towards the anode, the longer oligonucleotides migrating at a faster rate. This is as expected for molecules that are essentially identical except for net charge (e.g. +4 vs −4 for 1 and d(Tp)$_4$T, respectively). The relative magnitudes of migration are similar, although not the same, for DNG and DNA with the same number of bases. This slight discrepancy could be due to the increased rigidity of the guanidyl verses the phosphodiester backbone, or to the phosphate moiety's mass which is 38 Daltons greater per linkage than a guanidyl linkage. Since the oligonucleotides are migrating mainly by charge, the difference in mass between DNG and DNA should have a negligible influence on their relative electrophoretic migrations. Thus, the difference in oligonucleotide backbone flexibility is likely the main factor in the differing migration of DNG vs DNA.

Figure 14A:
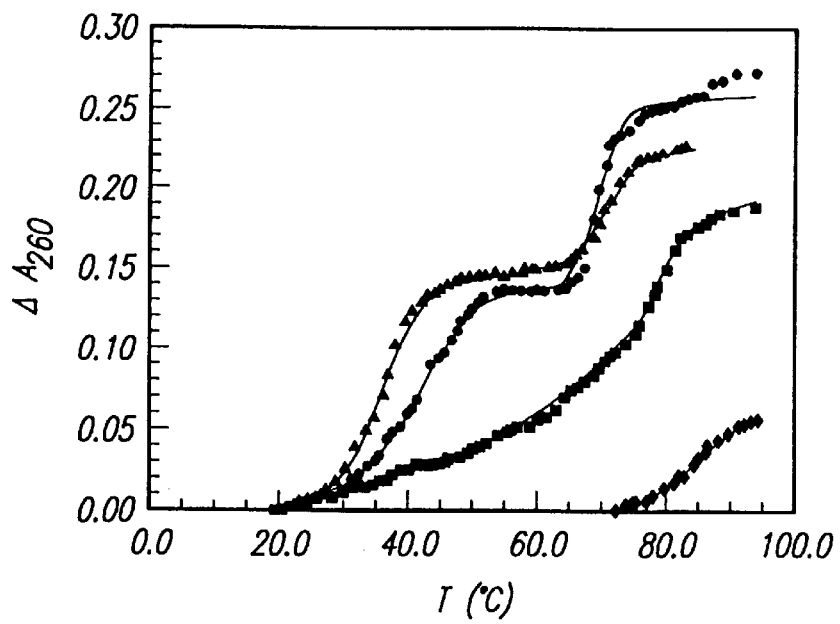
FIGS. 14A and 14B. (a) Plots of the change of A$_{260}$ vs T (°C.) for d(Tg)$_4$T-azido (1) in the presence of poly(da) at pH 7.0 (0.01 M K$_2$HPO$_4$). The ionic strength ($\mu$) was held constant at 0.12 (♦), 0.22 (■), 0.62 (●), and 1.20 (▲) with KCl. (b) Plots of the change of A$_{260}$ vs T (°C.) for 1 in the presence of p(dG)$_{12-18}$ (○), poly(dI) (□), poly(dC) (◇), or poly(dT) (△) are presented at $\mu$=1.2.
Figure 14B:
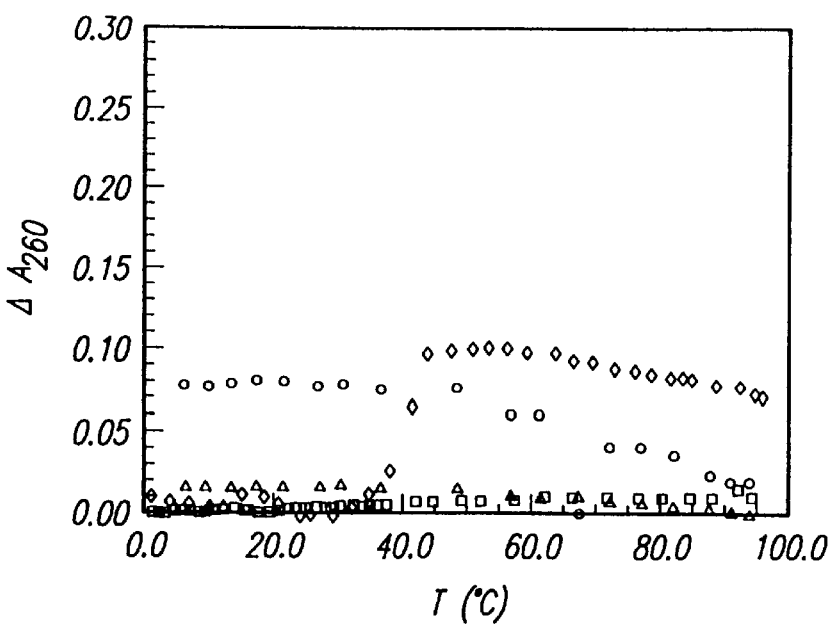

Thermal Denaturation Studies. In the thermal denaturation analysis of 1 bound to poly(dA), two distinct hyperchromic shifts were observed in the UV spectra ($\mu$=0.22, 0.62, and 1.2; FIG. 14a). In analogy to DNA and RNA thermal denaturation analysis (Riley, M., Maling, B. & Chamberlin, M. J. (1966) *J. Mol. Biol.* 20, 359–389.), these transitions correspond to the denaturation of a triple-helical hybrid at 68, 41, and 36° C. followed by denaturation of a duplex at 79, 70, and 71° C. At $\mu$=0.12, only one transition was seen centered at 85° C.; the thermal stability is apparently so great that the duplex structure does not denature at near boiling temperatures. This contrasts with the denaturation profiles of d(Tp)$_{15}$T bound to poly(dA); all have sharp, single denaturation transitions from duplex to single strands of DNA (39, 41, 52, and 56° C. at $\mu$=0.12, 0.22, 0.62, and 1.2, respectively; plots not shown). There was no hyperchromic shift in the UV spectra of a solution between ca. 5–93° C. which contained 1 and p(dG)$_{11-18}$, poly(dI), poly (dC), or poly(dT) (examined at both $\mu$=0.12 and 1.2, pH 7.0; FIG. 2b) that could be attributed to denaturation of a complex with 1 {although there was a hyperchromic shift centered at ca. 40° C. that was due to the denaturation of a poly(dC) complex with itself; this phenomenon has been reported (Akinrimisi, E. O., Sander, C. & Ts'o, P. O. P. (1963) *Biochemistry* 2, 340–344.)}. This is evidence against DNG binding to DNA in a nonspecific manner. Therefore, we conclude that electrostatic interactions dramatically increase the binding affinity of DNG to DNA without compromising Watson-Crick and Hoogsteen base-pair binding interactions.

Figure 15:
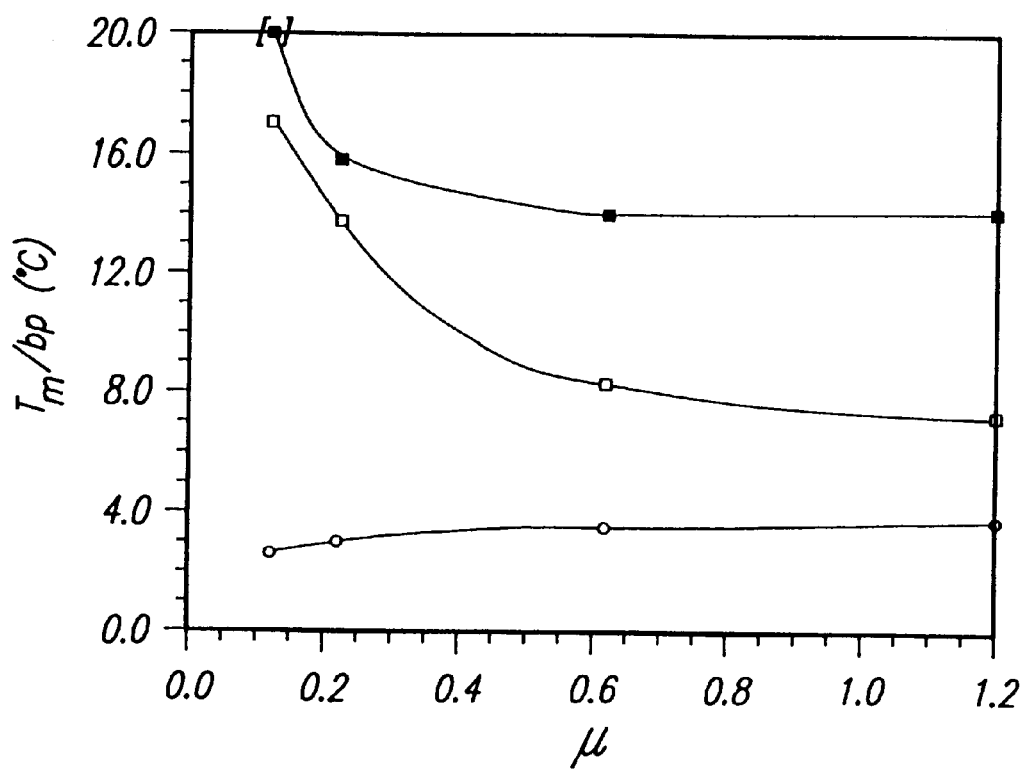
FIG. 15. A plot of T$_m$/(base pair) vs ionic strength ($\mu$) at pH 7.0 (0.01 M K$_2$HPO$_4$) from the denaturation of d(Tg)$_4$T-azido (□ and ■ for the first and second transitions, respectively) and d(Tp)$_{15}$T (○) complexed to poly(dA). The ionic strengths were held constant by using 0.11, 0.21, 0.61, and 1.19 M KCl. The data point at the lowest ionic strength for the T$_{m2}$ of DNG was simply taken as 100° C. because no hyperchromic transition was apparent by 93° C.

Ionic Strength Dependency Studies. In order to compare our thermal denaturation results for DNG with results obtained for DNA and modified oligonucleotides, denaturation data was reduced to the unit terms of $T_m$/base pair and, similarly, $T_m$/linkage. The plot of $T_m$/base pair vs ionic strength (FIG. 15) exemplifies the differences between the binding of DNG to DNA compared to the analogous DNA•DNA complex. Not only does thymidyl DNG have a tremendously greater affinity than thymidyl DNA for poly (dA) over a wide range of ionic strengths, but the effect of ionic strength is much more pronounced. Obviously, if electrostatic attraction stabilizes DNG•DNA complexes, the electrostatic force would be influenced by changing ionic strength. The observation that the effect of ionic strength has an opposite relationship for DNG complexes with DNA compared to DNA to DNA complexes is most noteworthy. Thus, while DNA•DNA duplexes become more stable with increasing ionic strength, triplexes and duplexes composed of both DNG and DNA become more stable with decreasing ionic strength. This should be expected since (i) increased salt concentration will effectively mask the opposing rows of negative charges on dsDNA allowing a more stable duplex and (ii) decreased salt concentration allows the oppositely charged backbones of the DNA hybrid complexes with DNG to be intimately salt paired, thus stabilizing these complexes. This effect has been alluded to with another positively charged oligonucleotide derivative (7) and suggests that electrostatic forces are responsible for the unique binding affinity of DNG to DNA.

A few examples of positively charged oligonucleotides have appeared in recent literature. Both the (ethylmorpholino)phosphoramidite (Letsinger, R. L., Singman, C. N., Histand, G. & Salunkhe, M. (1988) *J. Am. Chem. Soc.* 110, 4470–4471.) and the (aminomethyl) phosphonate (Fathi, R., Huang, Q., Syi, J.-L., Delaney, W. & Cook, A. F. (1994) *Bioconjugate Chem.* 5, 47–57.) oligonucleotide analogues contain positively charged ammonium groups connected via an alkyl linkage to the central phosphorous atom of the backbone moiety. DNG, on the other hand, maintains its positive charge in proper alignment to maximize it's interaction with the backbone of the negatively charged phosphates of the opposite strand. Both the (ethylmorpholino)phosphoramidite and the (aminomethyl) phosphonate derivatives' dimeric complexes with DNA have $T_m$ values in the range of 2–3° C./backbone linkage while the corresponding thymidyl DNG complexes have $T_m$ values of 14–>25° C./guanidyl linkage for duplex denaturation, depending on the salt concentration. Finally, the guanidyl linkage of DNG, unlike the linkages of the (ethylmorpholino)phosphoramidite and (aminomethyl) phosphonate oligonucleotides, is achiral. The importance of this point becomes apparent when considering the Sp and Rp stereoisomers of (aminomethyl)-phosphonate oligonucleotides which were shown to have vastly differing affinities for complementary DNA (Fathi, R., Huang, Q., Syi, J.-L., Delaney, W. & Cook, A. F. (1994) *Bioconjugate Chem.* 5, 47–57.).

From the above discussion, the following conclusions can be drawn about DNG: (i) DNG has a positively charged backbone that differentiates it from DNA; (ii) thymidyl DNG is specific for its complementary adenine tracts and not for guanidine or cytosine tracts; (iii) due to electrostatic attractions, DNG binds to DNA with a much greater affinity than DNA to DNA or other known modified oligonucleotides to DNA; and (iv) the thermal stability of DNA hybrid structures with DNG is influenced by changing salt concentrations. At low ion strength ($\mu$=0.12), short oligomers of DNG will essentially bind irreversibly to target nucleic acid.

EXAMPLE 5

Materials and Methods

Synthesis. General procedures. All TLC was run with Merck silica gel 60 ($F_{254}$) plates. $^1$H NMR were obtained on a 200 or 500 MHz instrument in DMSO-$d_6$ at 25° C. unless otherwise specified. Chemical shifts (ppm) were referenced to DMSO (2.49 ppm). The following nomenclature is used: The guanidyl linkage of DNG oligonucleotides is specified by the letter g, whereas thiourea-linked oligonucleotides are specified by the letter t.

2-O-Isopropylidene-5-trifluoroacetamido-5-deoxy-a-D-xylofuranose (6). To a stirred solution of 5-amino-5-deoxy-1,2-O-isopropylidene-a-D-xylofuranose$^5$ (20 g, 105.8 mmol) in 250 ml of dry $CH_2Cl_2$, cooled to 0° C., was added triethylamine (15 ml) followed by dropwise addition of trifluoroacetic anhydride (15 ml, 106.2 mmol). The reaction solution was stirred for 20 minutes with continued cooling. The $CH_2Cl_2$ was evaporated off and the residue was suspended in 500 ml of water. The aqueous layer was extracted with hexane (2×150 ml). The hexane extracts were discarded and the aqueous suspension was extracted with ether (3×500 ml). The pooled ether extracts were dried over sodium sulfate and evaporated to afford a white solid: 24.3 g (81%) yield; m.p.=110° C. dec (slow darkening); TLC (ether/hexane, 2:1) $R_f$=0.37; IR (KBr) 3451, 3266, 3116, 1712, 1577 1390, 1217, 1191, 1151, 1070, 1025 cm$^{-1}$; $^1$H NMR (DMSO-$d_6$) d 9.52 (1 H, br t, amide proton), 5.83 (1 H, d, J=3.7 Hz, 1-H), 5.39 (1 H, d, J=4.9 Hz, 3-OH), 4.42 (1 H, d, J=3.7 Hz, 2-H), 4.17 (1 H, m, 4-H), 3.97 (1 H, m, 3-H), 3.40 (2 H, m, 5-Hs), 1.37 and 1.23 (6 H, 2×s, isopropylidene) HRMS (FAB) m/e 286.0905 (M+H)$^+$, calcd for $C_{10}H_{15}NO_5F_3$ 286.0902.

2-O-Isopropylidene-5-trifluoroacetamido-5-deoxy-3-O-trifluoromethanesulfonyl-a-D-xylofur-anose (7). To a cooled solution (0° C.) of 6 (24.3 g, 85.2 mmol) in 250 ml of dry $CH_2Cl_2$ containing 4-dimethylaminopyridine (25.2 g, 206.2 mmol) was added trifluoromethanesulfonic anhydride (31.5 ml, 187.2 mmol) by dropwise addition over a period of ca.

20 minutes. The reaction solution was stirred for an additional 20 minutes with continued chilling. Ether (125 ml) was added to the completed reaction and the resulting mixture was filtered. The filtrate was evaporated and the residue was crystallized from ethanol-water: 28.7 g (81%) yield; m.p.=83° C.; TLC (50% hexane in ether) $R_f$=0.50; IR (KBr) 3344, 1704, 1550, 1419, 1213, 1178, 1095, 993, 931 cm$^{-1}$; $^1$H NMR (DMSO-d$_6$) d 9.69 (1H, br t, amide proton), 6.08 (1 H, d, J=3.8 Hz, 1-H), 5.56 (1 H, d, J=2.1 Hz, 3-H), 4.95 (1 H, d, J=3.9 Hz, 2-H), 4.57 (1 H, m, 4-H), 3.46 (2 H, m, 5-Hs), 1.45 and 1.30 (6 H, 2xs, isopropylidene) HRMS (FAB) m/e 418.0399 (M+H)$^+$, calcd for C$_{11}$H$_{16}$NO$_7$F$_6$S 418.0395.

Azido-1,2-di-O-acetyl-5-trifluoroacetamido-3,5-dideoxy-b-D-ribofuranose (10). To a solution of 7 (26.3 g, 63.1 mmol) dissolved in 150 ml of dry DMSO was added sodium azide (24.4 g, 375 mmol) followed by ammonium chloride (24.4 g, 456 mmol). The reaction mixture was stirred at 70° C. for 45 minutes and then diluted with 400 ml of water and extracted with ethyl acetate (3×300 ml). The pooled extracts were dried over sodium sulfate and evaporated to afford a 1:1 mixture of 8 and 9. The mixture was dissolved in 400 ml of 88% formic acid and stirred at 50° C. for 1 hour. The formic acid was evaporated and the residue was coevaporated with n-butanol (2×250 ml) followed by toluene (2×250 ml). The remaining residue was dissolved in 350 ml of dry pyridine and 260 ml of acetic anhydride was added. The solution was stirred at 25° C. for 2.0 hours and then poured over 500 ml of ice-water. The mixture was extracted with ether (3×400 ml) and the pooled extracts were evaporated to dryness. The residue was dissolved in 300 ml of ethyl acetate and 30 g of silica gel was added. The ethyl acetate was evaporated and the dry silica gel was placed in a fritted filter funnel and rinsed with 500 ml of 30% hexane in ether. Residual amounts of pyridine were removed by washing the filtrate with 3% HCl solution (3×150 ml). The organic solution was treated with activated charcoal, filtered through celite, and evaporated to afford crude 10 (5.1 g, 24% yeild for the three-step conversion) which was used without further purification for the preparation of 11. An analytical sample was obtained by preparative TLC employing 33% hexane in ether as the mobile phase. TLC (33% hexane in ether) $R_f$=0.40; IR (KBr) 3338, 2117, 1752 1726, 1556, 1373, 1217, 1182 cm$^{-1}$; $^1$H NMR (CDCl$_3$) d 6.84 (2 H, br t, amide), 6.13 (1 H, s, 1-H), 5.33 (1 H, d, J=4.5 Hz, 2-H), 4.21 (1 H, m, 4-H), 3.92 (1 H, m, 3-H), 3.86–3.58 (2 H, m, 5-Hs), 2.18 and 2.09 (6 H, 2xs, acetates) HRMS (Electron Impact) m/e 354.0740 (M$^+$), calcd for C$_{11}$H$_{13}$N$_4$O$_6$F$_3$ 354.0787

3'-Azido-6-benzamido-2'-O-t-butyldimethylsilyl-5'-trifluoroacetamido-3',5'-dideoxyadenosine (12). A suspension of N$^6$-benzoyladenine (3.0 g, 12.5 mmol) was refluxed in 45 ml of hexamethyldisilizane containing 4.5 ml of trimethylsilyl chloride for 20 h excluding moisture. Excess solvents were distilled away from the homogenous solution in vacuo and the residue was dissolved in 40 ml of dry dichloroethane containing 10 (2.90 g, 8.19 mmol) and trimethylsilyl trifluoromethanesulfonate (2.6 ml, 14.4 mmol) was added. The reaction solution was stirred at reflux for 20 hours and then diluted with 10 ml of methanol followed by 100 ml of ethyl acetate. The organic solution was washed with 100 ml of water and the aqueous layer was extracted with ethyl acetate (2×100 ml). The pooled organic extracts were dryed over sodium sulfate and evaporated to dryness affording a mixture of 11 (TLC: 10% methanol in CH$_2$Cl$_2$; $R_f$=0.55) and unreacted N$^6$-benzoyladenine.

The mixture was dissolved in 30 ml of methanol and 15 ml of 6% aqueous K$_2$CO$_3$ solution was added. The resulting solution was stirred at 50° C. for 15 min. The reaction was monitored by TLC (10% methanol in CH$_2$Cl$_2$). During some runs, the reaction time was extended to insure reaction completion as judged by TLC analysis. The completed reaction was diluted with 100 ml of water and extracted with ethyl aceate (3×100 ml). The pooled organic extracts were dried over sodium sulfate and evaporated to afford a mixture of deacetylated 11 (TLC 10% methanol in CH$_2$Cl$_2$; $R_f$=0.48) and unreacted N$^6$-benzoyladenine.

The mixture was dissolved in 30 ml of dry DMF containing imidazole (1.85 g, 27.2 mmol) and tert-butyldimethylsilyl chloride (4.0 g, 26.5 mmol) was added. The reaction solution was stirred at 60° C. for 90 min. The DMF was evaporated off and the residue was chromatographed through a silica gel column eluting with ethyl acetate. The pooled product fractions were evaporated to afford 12 as a glass: 1.31 g (26% yield for the three-step process); m.p.=75° C. (dec); TLC (ethyl acetate/hexane, 3:2) $R_f$=0.38; IR (KBr) 3259, 2954, 2933, 2112, 1720, 1612, 1581, 1459, 1255, 1218, 1180, 1155, 840 cm$^{-1}$; $^1$H NMR (DMSO-d$_6$) d 9.70 (1 H, br t, trifluroracetamide) 8.76 and 8.72 (2 H, 2xs, adenine protons), 8.05 and 7.59 (5 H, dd and m, J=1.6 and 6.9 Hz for the dd, aromatic protons), 6.09 (1 H, d, J=5.2 Hz, 1'-H), 5.31 (1 H, t, J=5.4 Hz, 2'-H), 4.45 (1 H, t, J=5.1 Hz, 3'-H), 4.16 (1 H, m, 4'-H), 3.69 (2 H, m, 5'-Hs), 0.79 (9 H, s, t-butyl), –0.013 and –0.22 (6 H, 2xs, methyl protons). HRMS (FAB) m/e 606.2236 (M+H)$^+$, calcd for C$_{25}$H$_{31}$N$_9$O$_4$F$_3$Si 606.2220

5'-Acetamido-3'-amino-2'-O-t-butyldimethyl-silyl 3',5'-dideoxyadenosine (2). A soution of 12 (1.20 g, 1.98 mmol), dissolved in 20 ml of 50% ammonium hydroxide in ethanol, was stirred in a sealed tube at 25° C. for 12 h. The solvents were removed in vacuo to afford crude 13, which was dissolved in 20 ml of dry DMF containing 0.28 ml of triethylamine. The solution was cooled in an ice-bath and acetyl chloride (0.14 ml, 1.98 mmol) was added dropwise. The resulting solution was stirred with continued chilling for 10 min. DMF was removed in vacuo and the residue was chromatographed through a silica gel column eluting with 10% methanol in ethyl acetate. The pooled product fractions were evaporated to afford 14 as a glass which was used directly in the following step.

A solution of 14 was dissolved in 20 ml of 50% aqueous pyridine and the solution was saturated with H$_2$S gas at 25° C. The reaction vial was sealed and the solution was allowed to stir at 25° C. for 12 h. Methanol (10 ml) was added to the completed reaction and the resulting solution was filtered. The filtrate was evaporated to give 2 as a solid: 432 mg; TLC (1-butanol/water/acetic acid, 5:3:2) $R_f$=0.56; IR (KBr) 2954, 2929, 2859, 1649, 1606, 1575, 1473, 1376, 1255, 1135, 838 cm$^{-1}$; $^1$H NMR (DMSO d$_6$) d 8.34 and 8.18 (2 H, 2xs, aromatic-Hs), 8.27 (1 H, t, J=5.74 Hz, amide N-H), 7.37 (2 H, br s, adenine NH$_2$), 5.91 (1 H, d, J=4.1 Hz, 1'-H), 4.70 (1 H, t, J=5.3 Hz, 2'-H), 3.86 (1 H, m, 4'-H), 3.43 (3 H, m, 3'- and 5'-Hs), 1.85 (3 H, s, acetyl Hs), 0.80 ( 9 H, s, t-butyl Hs), –0.04 and –0.13 (6 H, 2xs, silyl methyl Hs), HRMS (FAB) m/e 422.2320 (M+H)$^+$, calcd for C$_{18}$H$_{32}$N$_7$O$_3$Si 422.2336.

Azido-2'-O-t-butyldimethylsilyl-5'-isothio-cyano-3',5'-dideoxyadenosine (3). A solution of 12 (400 mg, 0.69 mmol), dissolved in 10 ml of 50% ethanol in ammonium hydroxide, was stirred in a sealed tube at 25° C. for 12 h. The solvents were removed in vacuo to give crude 13 which was dissolved in 10 ml of dry CH$_2$Cl$_2$ containing 0.14 ml of triethylamine and 1,3-dicyclohexylcarbodiimide (143 mg, 0.693 mmol). Carbon disulfide (0.50 ml) was added and the reaction solution was stirred at 25° C. for 10 min. The solution was evaporated and the residue was chromatographed through a silica gel column eluting with ethyl acetate. The pooled product fractions were evaporated to afford 3 as glass: 203 mg (66% yield for the two-step conversion); TLC (ethyl acetate) $R_f$=0.51; IR (film) 3332, 3182, 2952, 2856, 2206, 2107, 1658, 1602, 1577, 1255, 1153, 1085, 838 cm$^{-1}$; $^1$H NMR (DMSO-d$_6$) d 8.37 and 8.18 (2 H, 2×s, aromatic Hs), 7.38 (2 H, br s, adenine NH$_2$), 5.97 (1 H, d, J=6.0 Hz, 1'-H), 5.34 (1 H, t, J=5.8, 2'-H), 4.53 (1 H, m, 3'-H), 4.30–4.01 (3 H, m, 4'- and 5'-Hs), 0.75 (9 H, s, t-butyl Hs), −0.03 and −0.29 (6 H, 2×s, silyl methyl Hs). HRMS (FAB) m/e 448.1699 (M+H)$^+$, calcd for C$_{17}$H$_{26}$N$_9$O$_2$SSi 448.1699.

2'-Protected acetamido-r(A$_t$)A-azido (4). A solution of 2 (300 mg, 0.713 mmol) and 3 (319 mg, 0.713 mmol) dissolved in 3.0 ml dry DMF was stirred at 80° C. for 12 hours. The solution was evaporated and the residue was chromatographed through a silica gel column eluting with 15% methanol in ethyl acetate (containing 1% triethylamine). The product fractons were evaporated affording 4 as a solid: 502 mg (81% yield); m.p.=161° C. (dec) slow darkening; TLC (30% methanol in ethyl acetate) R$_f$=0.54; IR (KBr) 3315, 3215, 2952, 2929, 2107, 1649, 1601, 1576, 1473, 1255, 1147, 1079, 839, 782 cm$^{-1}$; $^1$H NMR (DMSO d$_6$) d 8.41, 8.37, 8.18 and 8.17 (4 H, 4×s, aromatic Hs), 8.23 (1 H, br t, amide N-H), 7.96 and 7.71 (2 H, 2×br peaks, thiourea N-Hs), 7.38 (4 H, br s, adenine NH$_2$), 5.94 and 5.88 (2 H, 2×d, J=6.5 and 3.2 Hz, 1'-Hs), 5.45–3.32 (10 H, 7×m, 2', 3', 4' and 5'-Hs), 1.83 (3 H, s, acetyl Hs), 0.74 and 0.71 (18 H, 2×s, t-butyl Hs), −0.04, −0.10, −0.15, −0.33 (12 H, 4×s, silyl methyl Hs). HRMS (FAB) m/e 869.3968 (M+H)$^+$, calcd for C$_{35}$H$_{57}$N$_{16}$O$_5$SSi$_2$ 869.3957.

2'-protected acetamido-r(A$_t$)$_3$A-azido (5). A solution of 4 (500 mg, 0.576 mmol) dissolved in 8.0 ml of 50% aqueous pyridine was saturated with H$_2$S (g) at 25° C. The resulting solution was stirred in a sealed tube for 12 h. TLC analysis (1-butanol/water/acetic acid, 5:3:2; R$_f$=0.68) indicated that the reaction was complete. The solution was degassed with argon and filtered. The filtrate was evaporated affording the 3'-amino dimer which was dissolved in 3.0 ml of dry DMF containing 3 (280 mg, 0.627 mmol) and subjected to another coupling reaction as described for the preparation of 4. The trimer-azido was precipitated from isopropanol-ether after evaporation of the DMF (376 mg yield). The supernatent was evaporated to dryness and an additional crop of product was obtained by precipitation of the residue from ether-hexane (186 mg yield). Total yield: 562 mg (76%); TLC (1-butanol/water/acetic acid, 5:3:2); R$_f$=0.83.

The trimer-azido (550 mg, 0.427 mmol) was reduced with H$_2$S (g), as described above, to the amino derivative which was reacted with a slight excess of 3. The tetramer-azido (5) was precipitated from 2-propanol-ether after removal of DMF: 482 mg (92%) yield; m.p.>160° C. (slow dec), TLC (1-butanol/water/acetic acid, 5:3:2) R$_f$=0.83; IR (KBr) 3195, 2954, 2931, 2107, 1641, 1599, 1577, 1544, 1473, 1255, 1126, 1089, 838 cm$^{-1}$; $^1$H NMR (DMSO-d$_6$, 60° C.) d 8.35, 8.34, 8.33 and 8.18 (8 H, 5×s, aromatic Hs), 7.94 and 7.52 (7 H, 2×m, amide N-H and thiourea N-Hs), 7.15 (8 H, br s, adenine NH$_2$), 5.94 and 5.87 (4 H, m and d, J=3.3 Hz for the d, 1'-Hs), 5.44–3.06 (20 H, t and 5×m, 2', 3' and 5'-Hs), 1.84 (3 H, s, acetomido CH$_3$), 0.77, 0.75, 0.72 and 0.70 (36 H, 4×s, t-butyl Hs), −0.02, −0.05, −0.09, −0.12, −0.14, −0.16 and −0.26 (24 H, 7×s, silyl methyl Hs); MS (FAB) m/e 1713.4 (M+H)$^+$, calcd for C$_{69}$H$_{111}$N$_{30}$O$_9$S$_3$Si$_4$ 1713.2.

Acetamido-r(A$_g$)$_3$A-azido (1). Compound 5 (50 mg, 0.029 mmol) was added to a solution of 0.5 ml of DMF and 0.14 ml of peracetic acid solution [32% (wt/wt) in dilute acetic acid, Aldrich] previously cooled to 0° C. The resulting solution was stirred for 15 min at 0° C. The DMF was evaporated off under a stream of N$_2$ (g) and the residue was dissolved in 4.0 ml of dry DMF and saturated with anhydrous ammonia at 25° C. The reaction vial was sealed and the solution was stirred at 80° C. for 4.0 h. The DMF was evaporated off and the residue was dissolved in 5.0 ml of 30% DMF in THF. Tetrabutylammonium fluoride (0.88 ml) was added and the reaction solution was stirred for 1.0 h. The solution was evaporated to dryness and the solid residue was washed with ether (2×10 ml). The ether extracts were discarded and the remaining solid was triturated with water and collected affording 1 as a crude solid: 22 mg (63% crude yield for the three-step process). An analytical sample was prepared by preparative HPLC using an Alltech WCX cation-exchange column eluting with 1.0 M ammonium acetate buffer, pH 5.0. A suspension of crude 1 in water was rendered water-soluble by addition of dilute acetic acid before HPLC injection. The peak of longest retention time (6.5 min, flow rate=1.5 ml/min), which was also the major component, was isolated and the ammonium acetate was removed from the RNG sample by repetitive evaporations from water; IR (KBr) 3413, 2967, 2114, 1648 1564, 1413, 1093, 652 cm$^{-1}$; $^1$H NMR (D$_2$O, 50° C.) d 8.21–7.89 (8 H, 7×s, aromatic Hs), 6.08, 6.01, 5.93 (4 H, d and 2×s, J=4.5 Hz for the d, 1'-Hs), 5.19 and 4.83 (4 H, t and m, J=5.5 Hz for the t, 2'-Hs), 4.55, 4.53, 4.52 and 4.39, (4 H, 4×m, 3'-Hs) 4.43, 4.35, 4.30 and 4.15 (4 H, 4×m, 4'-Hs), 3.92, 3.79, 3.76, 3.51, 3.50, 3.48 and 3.38 (8 H, 7×m, 5'-Hs), 1.91 (3 H, s, acetomido CH$_3$); MS (FAB) m/e 1204.48 (M+H)$^+$, calcd for C$_{45}$H$_{58}$N$_{33}$O$_9$ 1204.51

Molecular Modeling. Model building was performed as previously described. (Dempcy, R. O., Almarsson, O. & Bruice, T. C. (1994) Proc. Natl. Acad. Sci. USA 91, 7864–7868; Browne, K. A., Dempcy, R. O. & Bruice, T. C. (1995) Proc. Natl. Acad. Sci. USA 92, 7051–7055.) Prior to the minimizations, sodium ions (charge, +1.0) were placed adjacent to the phosphate moieties, and chloride ions (charge −1.0) were placed near the guanidinium groups. The CHARMM residue topology file was modified for the adenosyl RNG and termini to construct and parameterize the proposed structural system for the energy minimization calculations. Helical parameters for the minimized structure were analyzed using the NEWHEL93 program (Prive, G. G., Yanagi, K. & Dickerson, R. E. (1991) J. Mol. Biol. 217, 177–199). Calculation of the major and minor groove widths were based on the shortest distances between the phosphate phosphorous and the guanidinium carbon atoms across the major and minor grooves.

Synthesis. The general synthetic strategy for the formation of adenosyl RNG oligomers is similar to that described for the preparation of DNG oligomers. A thiourea-linked RNG dimer was formed by the reaction of a 5'-terminal residue, the adenosine 3'-amino derivative (2) (Scheme 3) and the 5'-isothiocyanate derivative (3). Chain extension proceeded via a two-step process involving hydrogen sulfide mediated reduction of the 3'-azido moiety to the amine, followed by an additional coupling reaction with a slight excess of 3. After construction of an oligomer of desired length, the thiourea linkages were converted to guanidinium linkages by a two-step process involving oxidation of the thiourea moiety to the aminoiminosulfonic acid derivative with peracetic acid and amination with anhydrous ammonia in dry DMF. The 2'-silyl ether groups, present on the RNG oligomer, were then removed using tetrabutylammonium fluoride. Final purification was performed by preparative HPLC using a cation-exchange column employing 1.0 M ammonium acetate buffer, pH 5.0, as the mobile phase.

The coupling intermediates 2 and 3 were prepared from a common synthetic pathway starting with 5-amino-5-deoxy-1,2-O-isopropylidene-a-D-xylofuranose (Scheme 4). The amine was protected as the trifluoroacetamide group before conversion of the 3-position to the azide. Thus, treatment of 6 with trifluoromethanesulfonic anhydride produced the 3-O-triflate derivative (7) which was then allowed to undergo an S$_N$2 displacement reaction with ammonium azide in DMF, forming the 3-azido derivative (8). The elimination product (9) was also formed in this reaction. The ratio of the substitution vs elimination products was determined to be approximately 1:1 by $^1$H NMR analysis. A similar product ratio was previously observed for the preparation of 3-azido-1,2-O-isopropylidene-5-O-(4-methylbenzoyl)-3-deoxy-alpha-D-ribofuranose (Ozols, A. M., Azhayev, A. V., Dyatkina, N. B., Krayevsky, A. A. (1980) *Synthesis* 7 557–559.) Isolation of the desired product was not performed at this point as the elimination product was conveniently removed after two subsequent steps.

Purination at the C-1 position utilizing Vorbruggen methodology necessitates the presence of a 1, 2-diacyl moiety. Thus, acid-catalyzed removal of the 1, 2-isopropylidene group with eighty eight percent formic acid solution was followed by acylation of the resulting diol with acetic anhydride in pyridine, yielding the b-1,2-diacetyl derivative (10) as the predominent product. Isolation of 8 was achieved by filtering the residue through silica gel with 30% hexane in ether. The elimination product decomposed during the formic acid treatment to a highly polar species which was retained on the silica gel.

Incorporation of a purine base at the C-1 position, using standard Vorbruggen reaction conditions (Vorbruggen, H., Nieballa, V., Krolikiewicz, K., Bennua, B., Hofle, G. In *Chemistry and Biology of Nucleosides and Nucleotides*, eds. Harmon, R. E., Robins, R. K., Townsend, L. B. (academic press, New York), pp. 251–265) resulted from the reaction of 10 with presilylated $N^6$-Benzoyladenine in the presence of trimethylsilyl triflate (Scheme 5). Formation of an intermediate ribofuranosyl carbocation is assisted by the neighboring effect of the 2'-acetyl group which attacks the a-position of C-1. Subsequent attack of the purine base can only occur at the b-position.

Regioselective ribosylation at the N-9 position of the purine ring is predicted to be the thermodynamic product. After the course of a 22 hour reaction time, only one nucleoside product (11) was detected. UV spectral analysis of the subsequent product (2) presented a UV maxima at 260 nm.

A concern of ours pertained to a possible intramolecular reaction of the free 2'-hydroxyl at the central carbon of the 3'-5' backbone after oxidation of the thiourea group. Thus, the 2'-acetyl group was selectively removed under mild basic conditions employing 6% aqueous potassium carbonate solution. The free hydroxyl group was subsequently protected as the tert-butyldimethylsilyl ether (12). Deprotection of the amide protecting groups was accomplished with concentrated ammonium hydroxide in ethanol, affording the amino derivative (13).

At this point two seperate synthetic pathways emerge forming the 5'-terminal intermediate and the 3'-chain extending intermediate. The 5'-unit (2) was prepared by a two-step process involving capping of the 5'-amino group of 13 as the acetamide (later synthetic strategies will involve connection of this amino group to a polymer for solid-support synthesis), followed by reduction of the 3'-azido moiety to the amine with hydrogen sulfide gas in aqueous pyridine. The 3'-chain extending intermediate (3) was prepared by treating 13 with carbon disulfide in the presence of 1,3-dicyclohexyl-carbodiimide. The resulting 5'-isothiocyanate derivative (3) was conveniently purified by flash chromatography.

The cationic nature of 1 was confirmed by its retention on a cation-exchange HPLC column. The $^1$H NMR spectrum of 1 identifies four adenosine moieties present in equal ratios. The 5'-terminal acetamido methyl protons are presented at 1.91 ppm. The presence of the 3'-azido terminal moiety was confirmed by an IR absorbance at 2114 cm$^{-1}$. Mass spectral analysis of 1 provided the correct mass of 1204.48 (M+H)$^+$.

Model of RNG (RNA)$_2$ triple helix. FIG. 16 shows the triple helix structure $(\text{Up})_9\text{U}\cdot\text{r}(\text{A}_g)_9\text{A}\cdot(\text{Up})_9\text{U}$, generated using QUANTA and the molecular mechanics program CHARMM. The sugar of the RNG strand is in the O4'-endo and C1'-exo conformation with the exception of the 3'-azido terminal residue, which is in the C1'-endo conformation. The sugar of the RNA strands is C1'-exo with the exception of the 3'-terminal ribose, which is O4'-endo. This is suggestive of a B-type nucleotide oligomer structure as is the 3.25 Å axial rise and 30.7° turn angle, as well as the 11.7 residue helical turn. The hydrogen bonds between the Watson-Crick and Hoogsteen base pairs are all maintained at 1.8 and 1.9 Å from donor to acceptor atoms. Counterions remained proximal to their respective charged groups. The major groove width contracts by 0.8 Å and the minor groove contracts by 0.2 Å, compared with a RNA triplex structure (Saenger, W. Principles of Nucleic Acid Structure (Springer-Verlag), 1984). The contractions are caused by electrostatic attractions between the positively charged RNG backbone and the negatively charged RNA backbone.

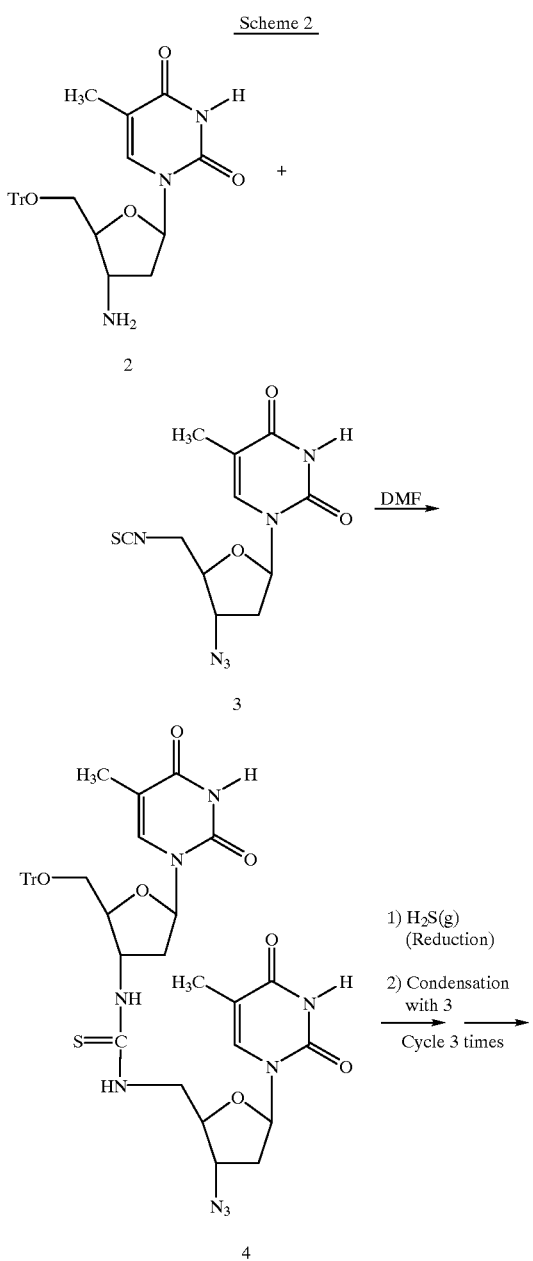

Scheme 2

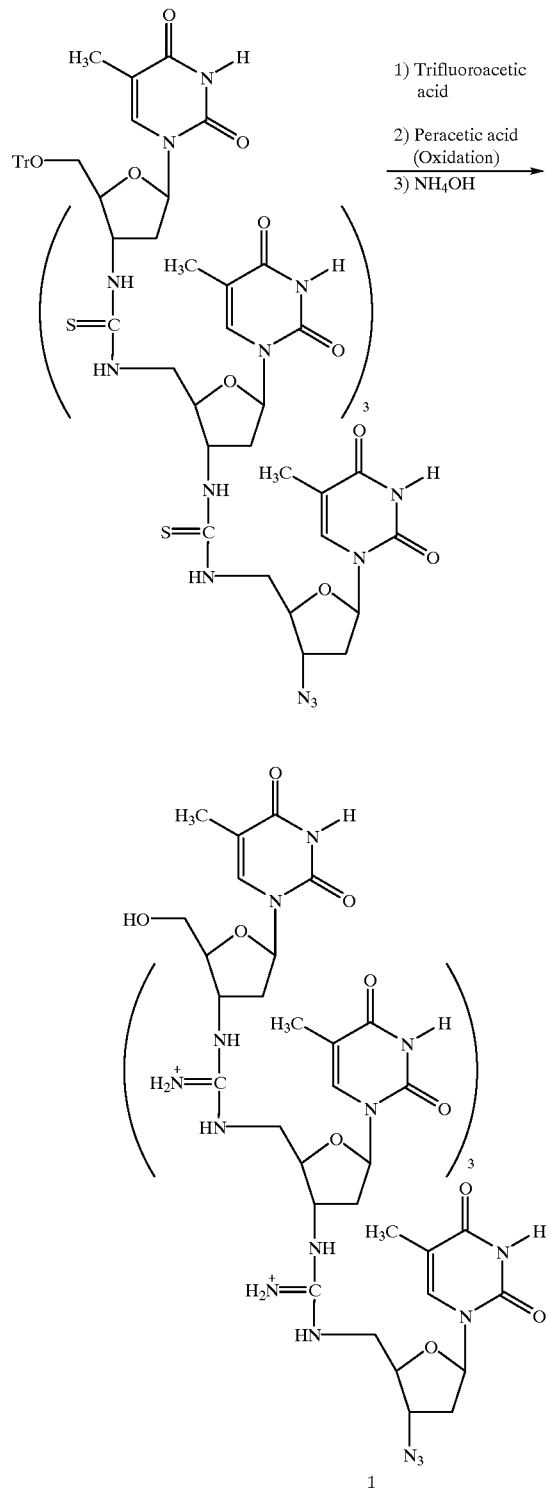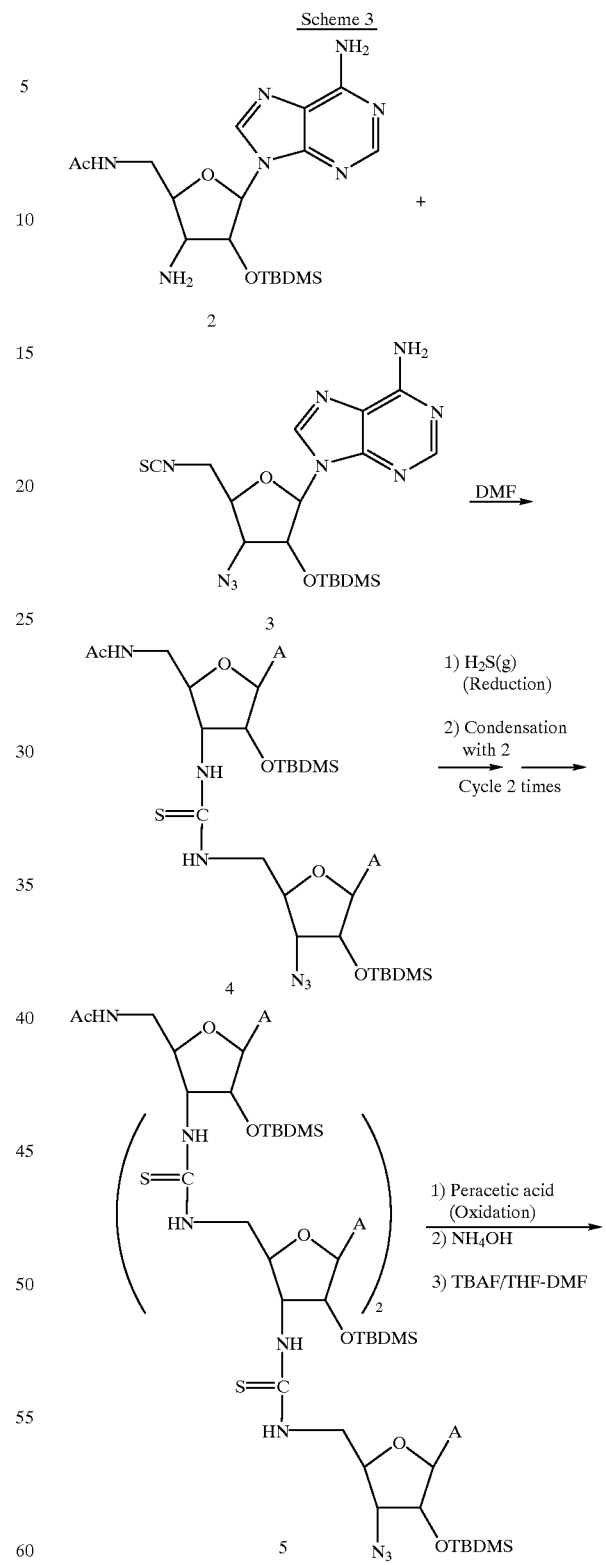

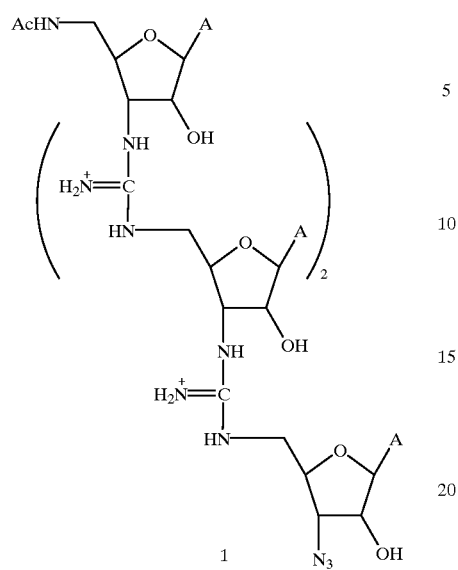
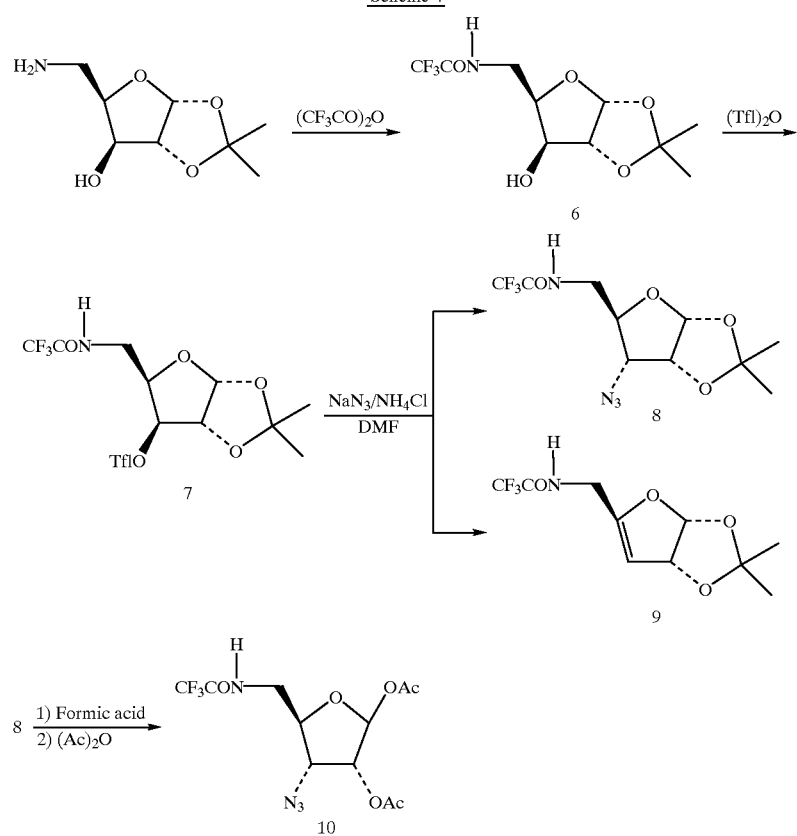

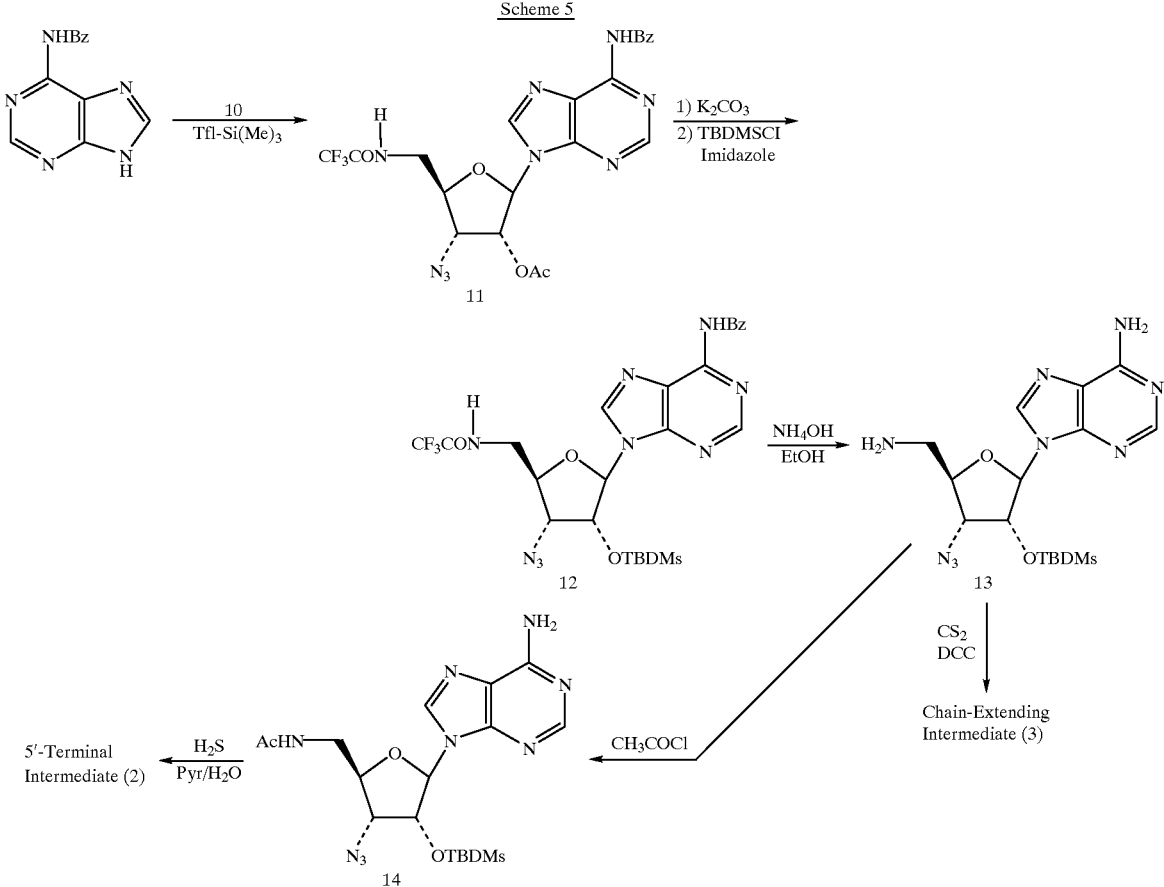

What is claimed is:

1. A cationic polynucleoside chain having multiple ribonucleosides, the nucleosides being coupled together by positively charged guanidyl linkages.

2. An antisense molecule of claim 1.

3. The polynucleoside of claim 1, wherein the polynucleoside is a heteromer.

4. The polynucleoside of claim 1, wherein the polynucleoside is a homomer.

5. The ribonucleic guanidinium (RNG) molecule of claim 2.

6. The RNG molecule of claim 5, wherein the nucleoside sequence is substantially complementary to a gene sequence.

* * * * *